United States Patent
Wang et al.

(10) Patent No.: US 10,702,513 B2
(45) Date of Patent: Jul. 7, 2020

(54) METHODS OF TREATING PAIN AND INDUCING ANALGESIA

(71) Applicant: NEW YORK UNIVERSITY, New York, NY (US)

(72) Inventors: Jing Wang, New York, NY (US); Edward Ziff, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 253 days.

(21) Appl. No.: 14/401,202

(22) PCT Filed: May 24, 2013

(86) PCT No.: PCT/US2013/042572
§ 371 (c)(1),
(2) Date: Nov. 14, 2014

(87) PCT Pub. No.: WO2013/177484
PCT Pub. Date: Nov. 28, 2013

(65) Prior Publication Data
US 2015/0125441 A1 May 7, 2015

Related U.S. Application Data

(60) Provisional application No. 61/750,504, filed on Jan. 9, 2013, provisional application No. 61/651,107, filed on May 24, 2012.

(51) Int. Cl.
| | |
|---|---|
| A61K 31/453 | (2006.01) |
| A61K 45/06 | (2006.01) |
| A61K 31/4015 | (2006.01) |
| A61K 31/275 | (2006.01) |
| A61K 31/42 | (2006.01) |
| A61K 31/7105 | (2006.01) |
| A61K 31/18 | (2006.01) |

(52) U.S. Cl.
CPC .......... A61K 31/453 (2013.01); A61K 31/18 (2013.01); A61K 31/275 (2013.01); A61K 31/4015 (2013.01); A61K 31/42 (2013.01); A61K 31/7105 (2013.01); A61K 45/06 (2013.01)

(58) Field of Classification Search
None
See application file for complete search history.

(56) References Cited

PUBLICATIONS

Scott, et al., "Predicting dissatisfaction following total knee replacement: a prospective study of 1217 patients." J. Bone Joint Surg Br 2010; 92: 1253-8.
Edwards, et al., "Catastrophizing and depressive symptoms as prospective predictors of outcomes following total knee replacement." Pain Res Manag 2009; 14: 307-11.
Dworkin, et al., "Clinical aspects of depression in chronic pain patients." Clin J. Pain 1991; 7: 79-94.
Romano et al., "Chronic pain and depression: does the evidence support a relationship?" Psychol Bull 1985; 97: 18-34.
Rieckmann, et al., "Depression vulnerabilities in patients with different levels of depressive symptoms after acute coronary syndromes." Psychother Pschother Psychosom 2006; 75: 353-61.
Serulle, et al. "A GluR1-cGKII interaction regulates AMPA receptor trafficking." Neuron 2007; 56: 670-688.
Miller, et al., "Comorbid chronic pain and depression: who is at risk?" J Pain 2009; 10: 619-627.
Wang, et al., "A single subanesthetic dose of ketamine relieves depression-like behaviors induced by neuropathic pain in rats." Anesthesiology 2011; 115: 812-821.
Becerra, et al., "Signal valence in the nucleus accumbens to pain onset and offset." Eur J Pain 2008; 12: 866-869.
Geha, et al. "The brain in chronic CRPS pain: abnormal gray-white matter interactions in emotional and autonomic regions." Neuron 2008; 60: 570-581.
Gear, et al., "Pain-induced analgesia mediated by mesolimbic reward circuits." Journal of Neuroscience 1999; 19: 7175-7181.
Lammel, et al., "Projection-specific modulation of dopamine neuron synapses by aversive and rewarding stimuli." Neuron 2011; 70: 855-862.
Roitman, et al., "Nucleus accumbens neurons are innately tuned for rewarding and aversive taste stimuli, encode their predictors, and are linked to motor output." Neuron 2005; 45: 587-597.
Reynolds, et al., "Emotional environments retune the valence of appetitive versus fearful functions in nucleus accumbens." Nat Neurosci 2008: 11: 423-425.
Nestler, et al., "The mesolimbic dopamine reward circuit in depression." Biol Psychiatry 2006; 59: 1151-9.
Tokita, et al., "Roles of glutamate signaling in preclinical and/or mechanistic models of depression." Pharmacol Biochem Behav 2011.
Park, et al., "Par-4 links dopamine signaling and depression." Cell 2005; 122: 275-87.
Kable, et al., "The neurobiology of decision: consensus and controversy." Neuron 2009; 63: 733-745.
Fields, "Understanding how opioids contribute to reward and analgesia." Reg Anesth Pain Med 2007; 32: 242-246.
Sanacora, et al., "Towards a glutamate hypothesis of depression: an emerging frontier of neuropsychopharmacology for mood disorders." Neuropharmacology 2012; 62: 63-77.

(Continued)

Primary Examiner — Joanne Hama
Assistant Examiner — Jon M Lockard
(74) Attorney, Agent, or Firm — FisherBroyles, LLP; J. David Smith

(57) ABSTRACT

The present invention provides methods of treating and pharmaceutical compositions useful for treating a mood disorder or depressive symptoms associated with pain, inducing analgesia and treating pain in a subject by administering a pharmaceutically effective amount of an agent capable of one or more of increasing GluA1 level, expression, concentration, or biological activity, increasing calcium permeable AMPA (α amino-3-hydroxy-5-methylisoxazole-4-propionic acid) receptor (CPAR) level, expression, concentration, or biological activity or potentiating a CPAR current. The agent may be an AMPA potentiator or ampakine. The agent may increase AMPA receptor currents by slowing the deactivation of open channels and may be, for instance, 2-pyrrolidinone, 4-[2-(phenylsulfonylamino) ethylthio]-2,6-difluorophenoxyacetamide (PEPA) or LY451646. The agent may also be a protein, RNA or DNA product.

6 Claims, 11 Drawing Sheets

(56) References Cited

PUBLICATIONS

Gear, et al., "Pain-induced analgesia mediated by mesolimbic reward circuits." J. Neurosci 1999; 19: 7175-81.

Wood, "Mesolimbic dopaminergic mechanisms and pain control." Pain 2006; 120: 230-4.

Sanacora, et al., "Towards a glutamate hypothesis of depression: an emerging frontier of neuropsychopharmacology for mood disorders." Neuropharmacology, 2012.

Koike, et al., "Involvement of AMPA receptor in both the rapid and sustained antidepressant-like effects of ketamine in animal models of depression." Behav Brain Res 2011; 224: 107-11.

Ziff, "TARPs and the AMPA receptor trafficking paradox." Neuron 2007; 53: 627-33.

Greger, et al. "Molecular determinants of Ampa receptor subunit assembly." Trends Neurosci 2007; 30: 407-16.

Barry, et al. "Receptor trafficking and the plasticity of excitatory synapses." Curr Opin Neurobiol 2002; 12: 279-86.

Conrad, et al., "Formation of accumbens GluR2-lacking AMPA receptors mediates incubation of cocaine craving." Nature 2008; 454: 118-21.

Chourbaji, et al., "AMPA receptor subunit 1 (GluR-A) knockout mice model the glutamate hypothesis of depression." FASEB J 2008; 22: 3129-34.

Toth, et al., "Age-dependent effects of chronic stress on brain plasticity and depressive behavior." J. Neurochem 2008; 107: 522-32.

Tan, et al. "Changes in AMPA subunit expression in the mouse brain after chronic treatment with the antidepressant maprotiline: a link between noradrenergic and glutamatergic function?" Exp Brain Res 2006; 170: 448-56.

Conrad, et al., "Formation of accumbens GluR2-lacking AMPA receptors mediates incubation of cocaine craving." Nature 2008; 454: 118-121.

Sesack, et al., "Cortico-Basal Ganglia reward network: microcircuitry." Neuropsychopharmacology 2010; 35: 27-47.

Nishizaki, et al., "The aniracetam metabolite 2-pyrrolidinone induces a long-term enhancement in AMPA receptor responses via a CaMKII pathway." Brain Res Mol Brain Res 2002; 98: 130-134.

Liu, et al., "Ca2+-permeable AMPA receptors in synaptic plasticity and neuronal death." Trends Neurosci 2007; 30: 126-134.

Cull-Candy, et al., "Regulation of Ca2+-permeable AMPA receptors: synaptic plasticity and beyond." Curr Opin Neurobiol 2006; 16: 288-297.

Goncalves et al, "Neuropathic pain is associated with depressive behaviour and induces neuroplasticity in the amygdala of the rat." Experimental neurology 2008, 213: 48-56.

Hu et al, "Depression-like behaviour in rats with mononeuropathy is reduced by the CB2-selective agonist GW405833." Pain 2009; 143: 206-212.

Vikman, et al., "Switch to Ca2+-permeable AMPA and reduced NR2B NMDA receptor-mediated neurotransmission at dorsal horn nociceptive synapses during inflammatory pain in the rat." J Physiol 2008; 586: 515-527.

Clem, et al., "Calcium-permeable AMPA receptor dynamics mediate fear memory erasure." Science 2010; 330: 1108-1112.

Gu, et al., "Synaptic strengthening through activation of Ca2+-permeable AMPA receptors." Nature 1996; 381: 793-796.

Bellone, et al., "In utero exposure to cocaine delays postnatal synaptic maturation of glutamatergic transmission in the VTA." Nat Neurosci 2011; 14: 1439-1446.

Argilli, et al., "Mechanism and time course of cocaine-induced long-term potentiation in the ventral tegmental area." J Neurosci 2008; 28: 9092-9100.

Lynch, et al., "Ampakines and the threefold path to cognitive enhancement." Trends Neurosci 2006; 29: 554-562.

Jin, et al., "Mechanism of positive allosteric modulators acting on AMPA receptors." J Neurosci 2005; 25: 9027-9036.

Quirk, et al. "LY404187: a novel positive allosteric modulator of AMPA receptors." CNS Drug Rev 2002; 8: 255-82.

Li, et al. "mTOR-dependent synapse formation underlies the rapid antidepressant effects of NMDA antagonists." Science 2010; 329: 959-964.

Volkow, et al., "Dopamine in drug abuse and addiction: results of imaging studies and treatment implications." Arch Neurol 2007; 64: 1575-9.

Wise, "Dopamine, learning and motivation." Nat Rev Neurosci 2004; 5: 483-94.

Brischoux, et al., "Phasic excitation of dopamine neurons in ventral VTA by noxious stimuli." Proc Natl Acad Sci USA 2009; 106: 4894-9.

Ehlers, et al., "Diffusional trapping of GluR1 Ampa receptors by input-specific synaptic activity." Neuron 2007; 54: 447-60.

Carr, et al., "AMPA receptor subunit GluR1 downstream of D-1 dopamine receptor stimulation in nucleus accumbens shell mediates increased drug reward magnitude in food-restricted rats." Neuroscience 2010; 165: 1074-86.

He, et al. "Stabilization of Ca2+-permeable AMPA receptors at perisynaptic sites by GluR1-S845 phosphorylation." Nati Acad Sci U S A 2009; 106: 20033-8.

Weyerbacher, et al., "N-Methyl-D-aspartate receptor (NMDAR) independent maintenance of inflammatory pain." Pain 2010; 148: 237-46.

Esteban, et al., "PKA phosphorylation of AMPA receptor subunits controls synaptic trafficking underlying plasticity." Nat Neurosci, 2003; 6: 136-43.

Sun, et al., "Dopamine receptor stimulation modulates AMPA receptor synaptic insertion in prefrontal cortex neurons." J Neurosci 2005; 25: 7342-51.

Boehm, et al., "Synaptic incorporation of AMPA receptors during LTP is controlled by a PKC phosphorylation site on GluR1." Neuron, 2006; 51: 213-25.

Sekiguchi, et al., "A desensitization-selective potentiator of AMPA-type glutamate receptors." Br J. Pharmacol 2002; 136: 1033-41.

Duric et al., "Neurokinin-1 (NK-1) receptor and brain-derived neurotrophic factor (BDNF) gene expression is differentially modulated in the rat spinal dorsal horn and hippocampus during inflammatory pain." Mol Pain 2007; 3: 32.

Rumpel, et al., "Postsynaptic receptor trafficking underlying a form of associative learning." Science 2005; 308: 83-8.

Mitsushima, et al., "Contextual learning requires synaptic AMPA receptor delivery in the hippocampus." Proc Natl Acad Sci USA 2011; 108: 12503-8.

Carr, et al., "Effects of the MEK inhibitor, SL-327, on rewarding, motor- and cellular-activating effects of D-amphetamine and SKF-82958, and their augmentation by food restriction in rat." Pschopharmacology (Berl) 2009; 201: 495-506.

Altier, et al., "Intra-VTA infusions of the substance P analogue, DiMe-C7, and intra-accumbens infusions of amphetamine induce analgesia in the formalin test for tonic pain." Brain Res 1993; 628: 279-85.

Simmons, et al., "Up-regulating BDNF with an ampakine rescues synaptic plasticity and memory in Huntington's disease knockin mice." Proc Natl Aced Sci USA 2009; 106: 4906-11.

Vyklicky, et al., "Modulation of excitatory synaptic transmission by drugs that reduce desensitization at AMPA/kainate receptors." Neuron 1991; 7: 971-84.

Goff, et al., "A placebo-controlled add-on trial of the Ampakine, CX516, for cognitive deficits in schizophrenia." Neuropsychopharmacology 2008; 33: 465-72.

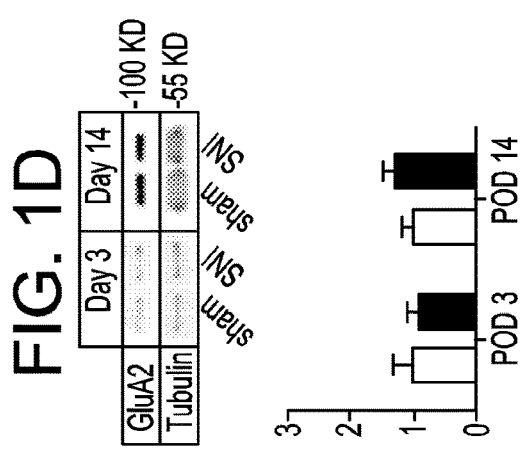
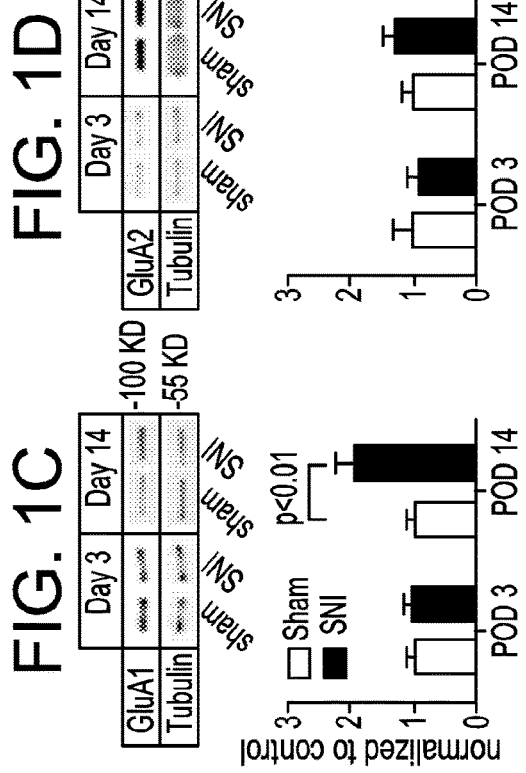
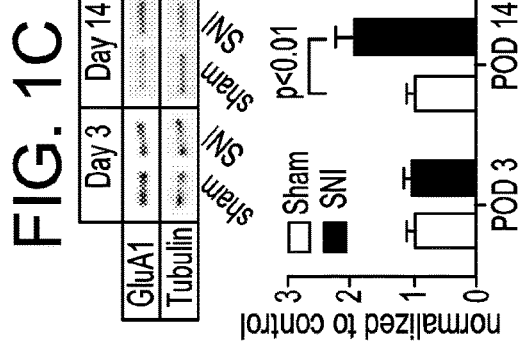
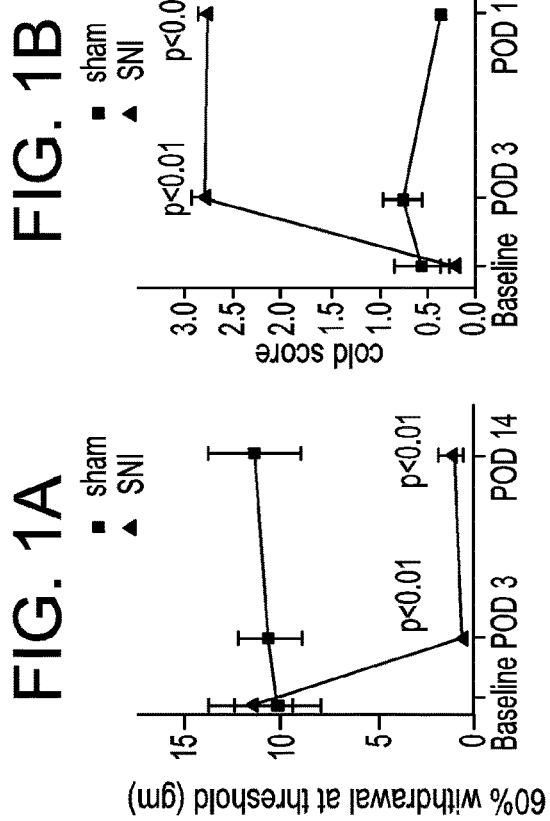
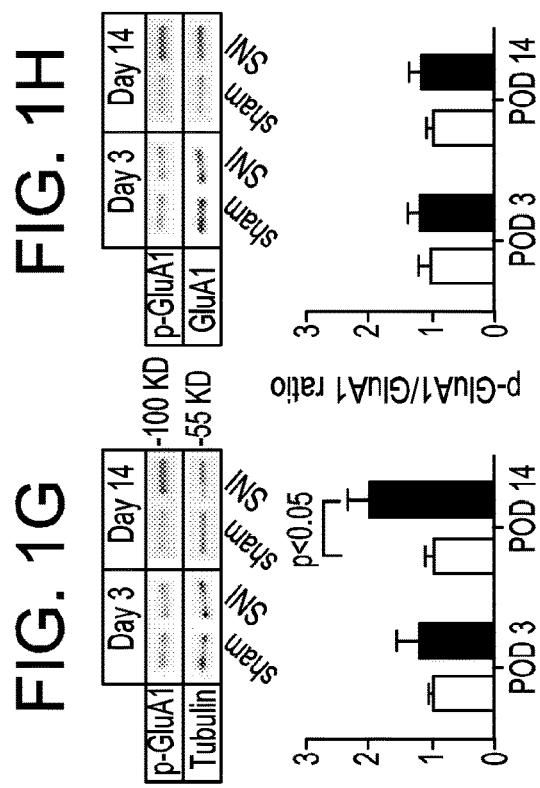
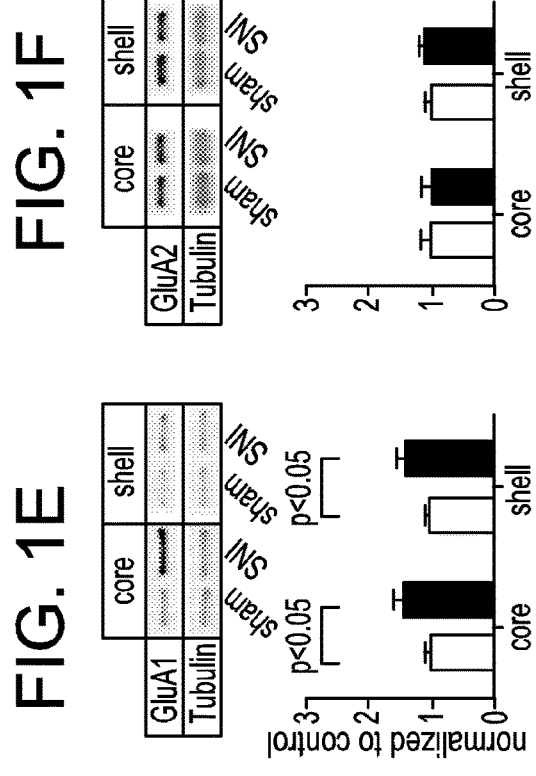

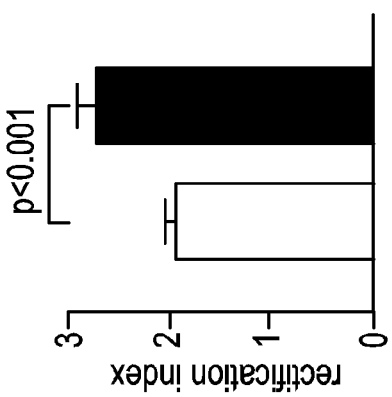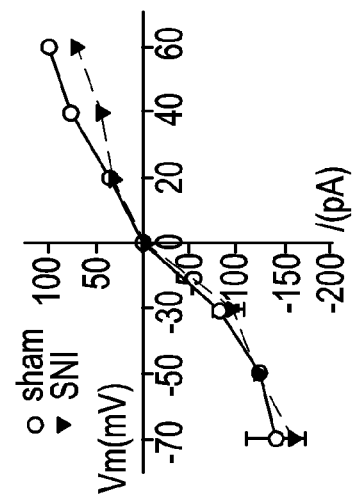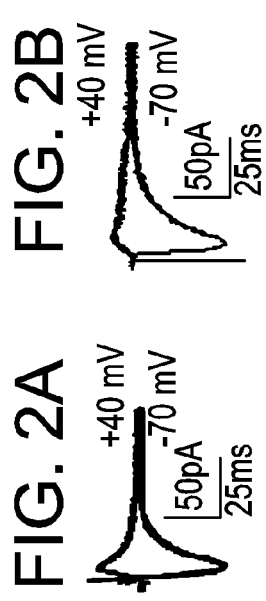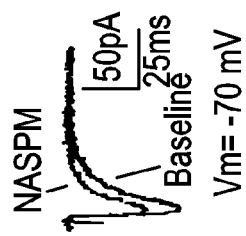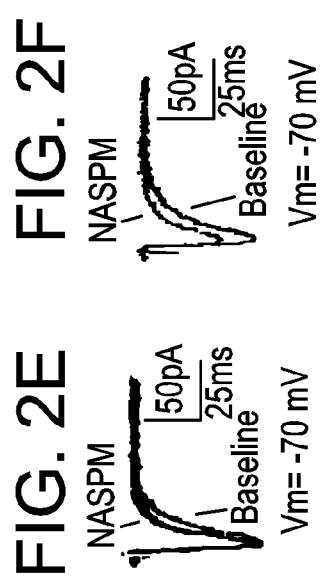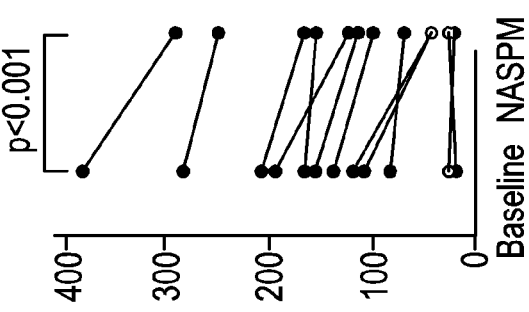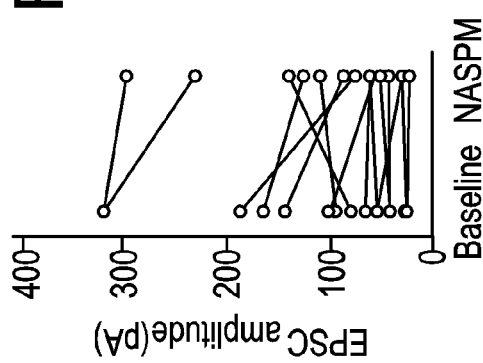

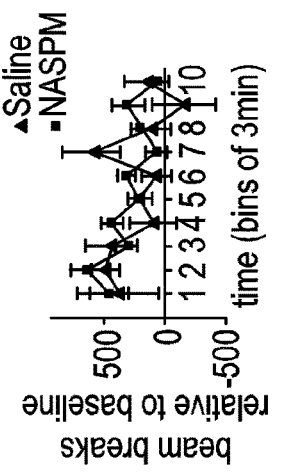 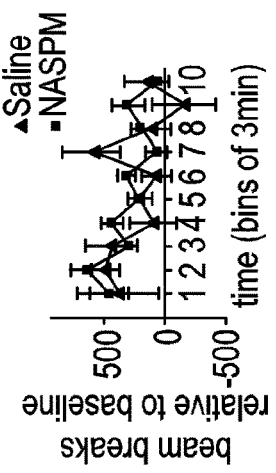 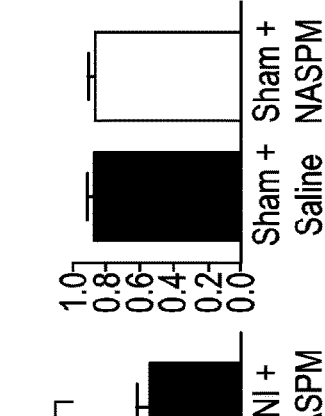
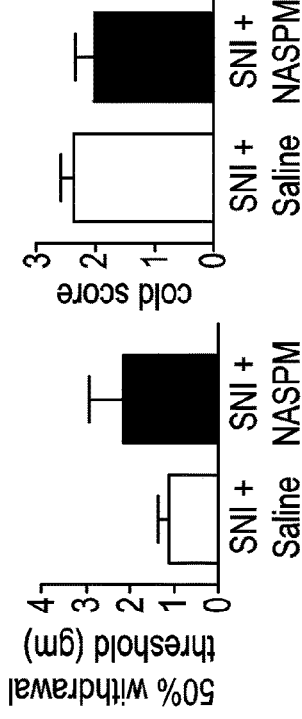 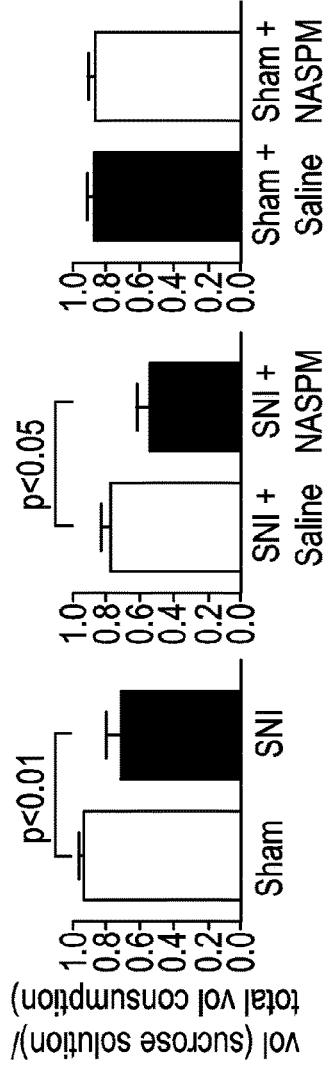
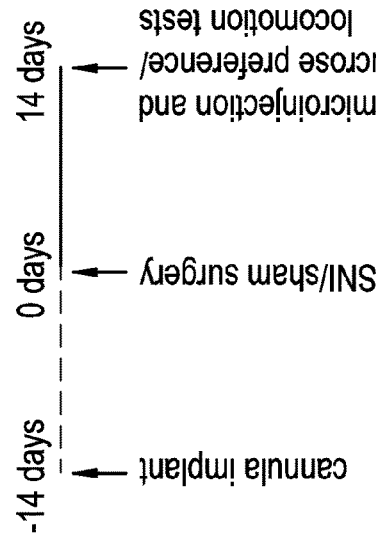 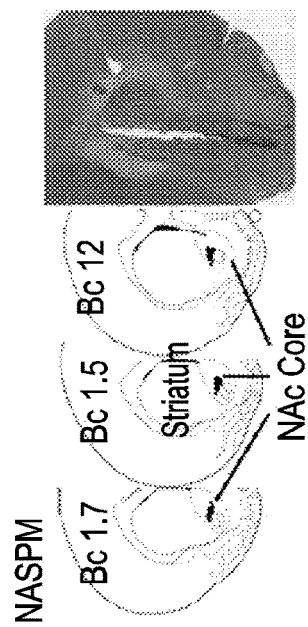
FIG. 3A  FIG. 3B  FIG. 3C  FIG. 3D  FIG. 3E  FIG. 3F  FIG. 3G  FIG. 3H

FIG. 5
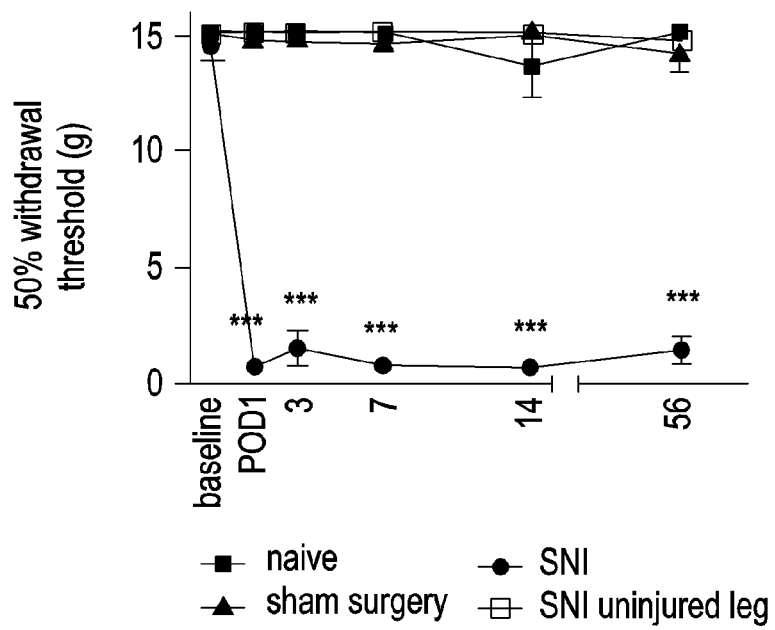
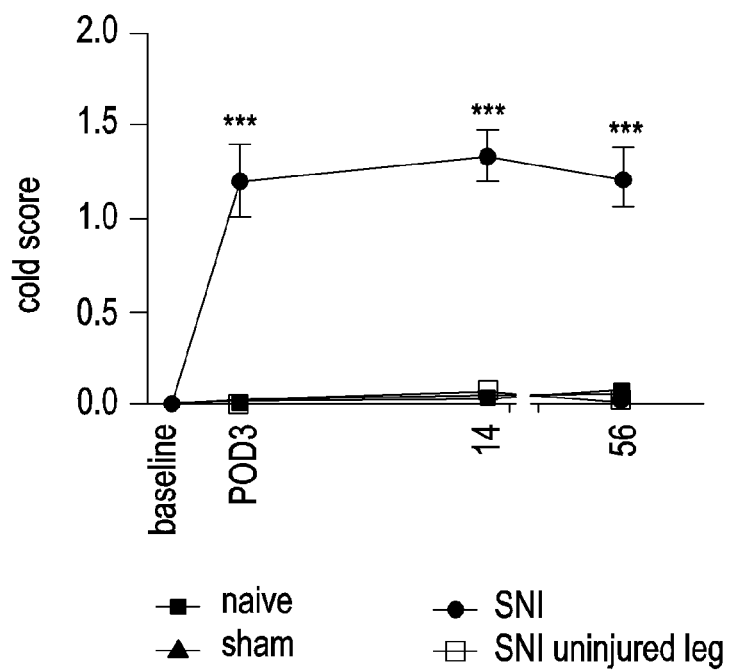

Hippocampus

Cerebellum

METHODS OF TREATING PAIN AND INDUCING ANALGESIA

CROSS REFERENCE TO RELATED APPLICATIONS

This application is the National Stage of International Application No. PCT/US2013/042572, filed May 24, 2013, which claims the benefit of priority to U.S. Provisional Application No. 61/651,107 filed May 24, 2012 and U.S. Provisional Application No. 61/750,504 filed Jan. 9, 2013, the disclosures of which are herein incorporated by reference in their entireties. Applicants claim the benefit of 35 U.S.C. § 120 as to the PCT application and the United States provisional application.

FIELD OF THE INVENTION

The present invention relates generally to treating mood disorders such as depression, particularly those associated with or subsequent to pain, such as chronic pain, inducing analgesia and treating pain.

BACKGROUND OF THE INVENTION

Pain is a major public health issue, affecting a third of Americans. Loss of function as the result of pain costs our healthcare system over 300 billion dollars annually. Pain is a common morbidity after surgery, and most pain patients suffer from depressed mood (Scott, et al., *J. Bone Joint Surg Br* 2010; 92: 1253-8; Edwards, et al., *Pain Res Manag* 2009; 14: 307-11 Dworkin, et al., *Clin J. Pain* 1991; 7: 79-94; Romano et al., *Psychol Bull* 1985; 97: 18-34 and Rieckmann, et al., *Psychother Pschother Psychosom* 2006; 75: 353-61). Pain-induced depression impairs rehabilitation and worsens surgical outcome.

Depression is also a common and debilitating affective feature of chronic pain (Dworkin, et al., *Clin J Pain* 1991; 7: 79-94; Miller, et al., *J Pain* 2009; 10: 619-627). Current analgesics focus on sensory pain symptoms, but drugs such as NSAIDs and opioids have significant side effects. Thus, better understanding of the regulation of depression in pain states will result in new treatments that focus on the depressive symptoms of pain to improve daily function. It was previously shown that chronic neuropathic pain directly induces depression-like behavior (Wang, et al., *Anesthesiology* 2011; 115: 812-821). The circuit and synaptic mechanisms for the affective expression of pain, however, remain unknown. The nucleus accumbens (NAc), traditionally thought as an integral element in the brain reward circuitry that processes appetitive stimuli, has recently been shown by human imaging and animal studies to be activated by pain and other aversive stimuli (Becerra, et al., *Eur J Pain* 2008; 12: 866-869; Geha, et al. *Neuron* 2008; 60: 570-581; Gear, et al., *Journal of Neuroscience* 1999; 19: 7175-7181; Lammel, et al., *Neuron* 2011; 70: 855-862; Roitman, et al., *Neuron* 2005; 45: 587-597; and Reynolds, et al., *Nat Neurosci* 2008: 11: 423-425). The role of the NAc in depression is also emerging (Nestler, et al., *Biol Psychiatry* 2006; 59: 1151-9; Tokita, et al., *Pharmacol Biochem Behav* 2011; and Park, et al., *Cell* 2005; 122: 275-87). Because of the critical function NAc serves in mediating hedonic and motivational behaviors (Kable, et al., *Neuron* 2009; 63: 733-745; Fields, *Reg Anesth Pain Med* 2007; 32: 242-246), its role as a potential link between pain and depression was examined. Glutamate signaling which plays an important role in depression (Sanacora, et al., *Neuropharmacology* 2012; 62: 63-77) has been poorly studied in the NAc in aversive states.

The nucleus accumbens (NAc) is a strong candidate brain region for regulating depression in postoperative and chronic pain states. Most neurons in the NAc are medium spiny neurons (MSNs), which express dopamine and glutamate receptors. Dopamine signaling has been shown to provide descending pain inhibition by the midbrain-spinal cord pathway (Gear, et al *J. Neurosci* 1999; 19: 7175-81; Wood, *Pain* 2006; 120: 230-4). Glutamate signaling in the NAc is poorly studied in pain states, but it features prominently in depression studies (Sanacora, et al., *Neuropharmacology* 2011; Tokita, et al., *Pharmacol Biochem Behav* 2011; Koike, et al., *Behav Brain Res* 2011; 224: 107-11).

A key glutamate signaling mechanism is the trafficking of α-amino-3-hydroxy-5-methyl-4-isoxazolepropionic acid (AMPA) receptors (Ziff, *Neuron* 2007; 53: 627-33). AMPA receptors bind glutamate to conduct excitatory post-synaptic currents, and they are tetramers formed by varying combinations of four subunits, GluA1, 2, 3 and 4. GluA1 and GluA2 are the most abundant subunits in the NAc. GluA2-lacking AMPA receptors form in the NAc when GluA1 expression is increased, and they are permeable to calcium (Greger, et al *Trends Neurosci* 2007; 30: 407-16). These calcium permeable AMPA receptors (CPARs) can regulate calcium-dependent synaptic plasticity. While GluA2 subunits constitutively traffic to synapses, GluA1 trafficking is activity-dependent and hence may respond to rewards (Barry, et al. *Curr Opin Neurobiol* 2002; 12: 279-86) or pain. Thus, tightly controlled GluA1 trafficking promotes the formation of CPARs in the NAc and provides synaptic plasticity to regulate behaviors (Conrad, et al., *Nature* 2008; 454: 118-21). GluA1 has been shown to modulate depressive symptoms. For example, GluA1 knockout mice display vulnerability to depression (Chourbaji, et al., *FASEB J* 2008; 22: 3129-34), and decreased GluA1 levels in the NAc have been reported in rats that exhibit depressive behavior (Toth, et al., *J. Neurochem* 2008; 107: 522-32), whereas increased GluA1 levels are found in the NAc with antidepressant treatments (Tan, et al. *Exp Brain Res* 2006; 170: 448-56). Studies in chronic pain or postoperative pain, however, have not examined the role of GluA1 in the NAc, and our study seeks to address this knowledge gap.

Glutamatergic AMPA (α amino-3-hydroxy-5-methylisoxazole-4-propionic acid) receptors mediate the majority of fast excitatory synaptic transmission in the brain. In the forebrain areas, AMPA receptors are heteromeric complexes assembled from mainly GluA1 and GluA2. The other two subunits of AMPA receptor, GluA3 and GluA4 express at relative lower levels. According to the new subunit nomenclature recommended by the International Union of Basic and Clinical Pharmacology (IUPHAR), these AMPA subunits are renamed as GluA1, GluA2, GluA3 and GluA4. Ampakines are a class of compounds known to enhance attention span and alertness, and facilitate learning and memory strongly interact with these receptors. Ampakines do not seem to have unpleasant, long-lasting side effects such as sleeplessness. They are currently being investigated as potential treatment for a range of conditions involving mental disability and disturbances such as Alzheimer's disease, Parkinson's disease, schizophrenia, Treatment-resistant depression (TRD) or neurological disorders such as Attention Deficit Hyperactivity Disorder (ADHD), among others. Ampakine activity has been established as one of the modes of action of the well established class of nootropics, the racetam drugs such as piracetam, aniracetam, oxiracetam and pramiracetam, however these drugs have multiple modes of action and produce only weak AMPA receptor activation. More recently developed ampakine compounds are much more potent and selective for the AMPA receptor target, and while none of the newer selective ampakine compounds have yet come onto the market, one compound CX717 is currently in Phase II clinical trials as of 2008. Four structural classes of ampakine drugs have been developed so far: the pyrrolidine derivative racetam drugs such as piracetam and aniracetam, the CX-series of drugs which encompass a range of benzoylpiperidine and benzoylpyrrolidine structures, benzothiazide derivatives such as cyclothiazide and IDRA-21, and biarylpropylsulfonamides such as LY-392,098, LY-404,187, LY-451,646 and LY-503,430. AMPAkines, however, have not been investigated in pain.

SUMMARY OF THE INVENTION

The present invention is based in part upon the discovery that increasing calcium permeable AMPA ($\alpha$ amino-3-hydroxy-5-methylisoxazole-4-propionic acid) receptor (CPAR) level, expression, concentration, or biological activity is found in the chronic and postoperative pain states, and that potentiating CPAR currents may be effective in reducing symptoms of depression such as depression occurring subsequent to or concurrent with pain, for example, chronic or postoperative pain, for inducing analgesia and for treating pain, for example, chronic or postoperative pain. As such, CPARs are a novel therapeutic target for treating depressive symptoms, such as, for instance, those associated with chronic or postoperative pain, for inducing analgesia and for treating pain, for example, chronic or postoperative pain.

In a first aspect, the present invention provides methods for treating a mood disorder or depressive symptoms associated with pain in a subject by administering a pharmaceutically effective amount of an agent capable of one or more of increasing GluA1 level, expression, concentration, or biological activity, increasing calcium permeable AMPA ($\alpha$ amino-3-hydroxy-5-methylisoxazole-4-propionic acid) receptor (CPAR) level, expression, concentration, or biological activity or potentiating a CPAR current. The mood disorder may be, for instance, depression or dysthymia, such as depression secondary to or concurrent with acute or chronic or postoperative pain. The agent may be an AMPA potentiator or ampakine. The agent may increase AMPA receptor currents by slowing the deactivation of open channels. 2-pyrrolidinone, 4-[2-(phenylsulfonylamino)ethylthio]-2,6-difluorophenoxyacetamide (PEPA), CX546 and LY451646 are such exemplary ampakines. The agent may also be administered in combination with one or more other antidepressants such as, for example, low-dose ketamine. The CPAR current may be increased 5%, 10%, 20%, 30%, 40%, 50%, 60%, 75%, 80%, 90%, two times, three times, four times, five times, ten times, twenty times, or even fifty or a hundred times more compared to control. The agent may be, for instance, a small molecule, a (coding or noncoding) RNA, a protein or an antibody.

In a second aspect, the present invention provides methods for inducing analgesia in a subject by administering a pharmaceutically effective amount of an agent capable of one or more of increasing GluA1 level, expression, concentration, or biological activity, increasing calcium permeable AMPA ($\alpha$ amino-3-hydroxy-5-methylisoxazole-4-propionic acid) receptor (CPAR) level, expression, concentration, or biological activity or potentiating a CPAR current. The subject may be suffering from a mood disorder or depressive symptoms. The analgesia may feature increased tolerance to cold, heat, or reduced perception of acute or chronic or postoperative pain. The agent may be an AMPA potentiator or ampakine. The agent may increase AMPA receptor currents by slowing the deactivation of open channels. 2-pyrrolidinone, 4-[2-(phenylsulfonylamino)ethylthio]-2,6-difluorophenoxyacetamide (PEPA), CX546 and LY451646 are such exemplary ampakines. The agent may also be administered in combination with one or more other analgesics. The CPAR current may be increased 5%, 10%, 20%, 30%, 40%, 50%, 60%, 75%, 80%, 90%, two times, three times, four times, five times, ten times, twenty times, or even fifty or a hundred times more compared to control. The agent may be, for instance, a small molecule, a (coding or noncoding) RNA, a protein or an antibody. The agent may be administered, for instance, systemically, and at a dose of, for instance, at least 1 mg/kg, 2 mg/kg, 5 mg/kg, 10 mg/kg, 20 mg/kg, or 50 mg/kg or more.

In a third aspect, the present invention provides methods for treating pain in a subject by administering a pharmaceutically effective amount of an agent capable of one or more of increasing GluA1 level, expression, concentration, or biological activity, increasing calcium permeable AMPA ($\alpha$ amino-3-hydroxy-5-methylisoxazole-4-propionic acid) receptor (CPAR) level, expression, concentration, or biological activity or potentiating a CPAR current. The subject may be suffering from a mood disorder or depressive symptoms. The pain may be acute or chronic or postoperative pain. The agent may be an AMPA potentiator or ampakine. The agent may increase AMPA receptor currents by slowing the deactivation of open channels. 2-pyrrolidinone, 4-[2-(phenylsulfonylamino)ethylthio]-2,6-difluorophenoxyacetamide (PEPA), CX546 and LY451646 are such exemplary ampakines. The agent may also be administered in combination with one or more other analgesics or pain medications. The CPAR current may be increased 5%, 10%, 20%, 30%, 40%, 50%, 60%, 75%, 80%, 90%, two times, three times, four times, five times, ten times, twenty times, or even fifty or a hundred times more compared to control. The agent may be, for instance, a small molecule, a (coding or noncoding) RNA, a protein or an antibody. The agent may be administered, for instance, systemically, and at a dose of, for instance, at least 1 mg/kg, 2 mg/kg, 5 mg/kg, 10 mg/kg, 20 mg/kg, or 50 mg/kg or more.

In a fourth aspect, the present invention provides methods of identifying an agent effective in treating a mood disorder or depressive symptoms associated with pain, inducing analgesia or treating pain in a subject by identifying an agent capable of one or more of increasing GluA1 level, expression, concentration, or biological activity, increasing calcium permeable AMPA ($\alpha$ amino-3-hydroxy-5-methylisoxazole-4-propionic acid) receptor (CPAR) level, expression, concentration, or biological activity or potentiating a CPAR current. The mood disorder may be, for instance, depression or dysthymia, such as depression secondary to or concurrent with acute or chronic or postoperative pain. The agent may be an AMPA potentiator or ampakine. The agent may increase AMPA receptor currents by slowing the deactivation of open channels. The CPAR current may be increased 5%, 10%, 20%, 30%, 40%, 50%, 60%, 75%, 80%, 90%, two times, three times, four times, five times, ten times, twenty times, or even fifty or a hundred times more compared to control. The agent may be, for instance, a small molecule, a protein or an antibody.

Agents such as small molecules, RNAs, proteins and antibodies may be identified by standard assay techniques known in the art as applied to identify those agents that increase GluA1 level, expression, concentration, or biological activity, increase CPAR level, expression, concentration, or biological activity or potentiate a CPAR current. The agent may be a protein, an antibody, a RNA, or a biologically active fragment, derivative or analog thereof.

In a fifth aspect, the present invention provides pharmaceutical compositions comprising a therapeutically effective amount of an agent effective in treating a mood disorder or depressive symptoms associated with pain, inducing analgesia or treating pain in a subject. The agent may be capable of one or more of increasing GluA1 level, expression, concentration, or biological activity, increasing calcium permeable AMPA (α amino-3-hydroxy-5-methylisoxazole-4-propionic acid) receptor (CPAR) level, expression, concentration, or biological activity or potentiating a CPAR current. The mood disorder may be, for instance, depression or dysthymia, such as depression secondary to or concurrent with acute or chronic or postoperative pain. The agent may be an AMPA potentiator or ampakine. The agent may increase AMPA receptor currents by slowing the deactivation of open channels. The CPAR current may be increased 5%, 10%, 20%, 30%, 40%, 50%, 60%, 75%, 80%, 90%, two times, three times, four times, five times, ten times, twenty times, or even fifty or a hundred times more compared to control. The agent may be, for instance, a small molecule, a RNA, a protein or an antibody.

Agents such as small molecules, proteins, RNAs and antibodies may be identified by standard assay techniques known in the art as applied to identify those agents that increase GluA1 level, expression, concentration, or biological activity, increase CPAR level, expression, concentration, or biological activity or potentiate a CPAR current. The agent may be a protein, an antibody, a RNA, or a biologically active fragment, derivative or analog thereof.

BRIEF DESCRIPTION OF THE FIGURES

FIG. 1 demonstrates that GluA1 upregulation in the NAc occurs with the development of chronic pain, representing a unique form of plasticity. Peripheral nerve injury leads to pain that lasted at least 14 days, as shown by mechanical and cold hypersensitivity (FIG. 1a,b). After pain induction, GluA1 levels are increased (by ~50%) in the synaptic fractions of the NAc (FIG. 1c, e). The level of GluA2 subunits, however, remained unchanged in the acute and chronic neuropathic pain states (FIG. 1d). These results show that chronic pain causes molecular changes in both core and shell sub-regions of the NAc. The core region is particularly interesting, where pain may serve as a chronic cue to give rise to behavioral modification such as resilience to depression. Phosphorylation at Ser845 was significantly increased (>50%) (FIG. 1e, f, g) in the NAc. This mechanism is important for the accumulation of functional GluA1 at the cell surface, and hence, this trafficking mechanism is conserved in the chronic pain state. The ratio of pGluA1/total GluA1, however, was not altered after SNI (FIG. 1h).

FIG. 2 demonstrates that calcium permeable AMPA receptors are indeed formed by the accumulation of GluA1 subunits. Medium spiny neurons were identified visually in the NAc core, and evoked excitatory postsynaptic currents (EPSCs) were recorded (FIG. 2i). When the current-voltage relationship of EPSCs was calculated (Conrad, et al., Nature 2008; 454: 118-121), MSNs from SNI-treated animals displayed a significant increase in inward rectification compared with control neurons (FIG. 2a-d). a, b represent current traces of EPCSs; c shows current voltage relationship for traces in a and b; d shows rectification index. In addition, bath application of NASPM reduced the amplitudes of EPSCs in neurons recorded from the SNI group, but not the control group (FIG. 2e-h). e and represent current traces in the presence and absence of NASPM; g and h tabulate the effects of NASPM on current amplitudes in 12-15 neurons. These results confirm biochemical findings of increased GluA1 levels and demonstrate that functional CPARs are specifically formed at NAc synapses in response to chronic neuropathic pain.

FIG. 3 demonstrates that CPARs in the NAc do not regulate sensory symptoms of pain, but they attenuate pain induced depression. a, schematic for the timeline of experiment. b, location of the NASPM injection in the core region of the NAc. Both sensory and depressive components of pain were evaluated after NASPM treatment. NASPM did not alter mechanical or cold hypersensitivity after SNI (FIG. 3c, d), suggesting that while CPARs in the NAc are formed in response to chronic pain, they are not necessary for the sensory transmission of the pain signal. The depressive feature of pain was assayed by a decreased sucrose preference on the sucrose preference test, a test classically used to assess depression. As shown previously (Wang et al, Anesthesiology, 2012), SNI caused a decrease in sucrose preference (FIG. 3f). NASPM produced a striking effect on the depression-like behavior of SNI-treated rats, as evidenced by a significant further decline in their already reduced sucrose preference (FIG. 3g). In contrast, sham-treated rats, lacking robust CPAR expression in their NAc did not show this depression-like behavioral response to NASPM (FIG. 3h). Thus, while CPARs are not necessary for sensory pain transmission, they enable a novel modulation of the depression-like behavior induced by chronic pain, through their regulation of synaptic function in the NAc. The specificity of the observed behavioral phenotype is further supported by a lack of change in locomotion after NASPM treatment (FIG. 3e).

FIG. 5 demonstrates that SNI induces chronic sensory hypersensitivity. (A) SNI treated rats develop mechanical hypersensitivity on injured legs starting on POD 1, lasting until POD56. *p<0.001, two-way ANOVA, with post-hoc Bonferroni tests. Naïve=14; sham=22; SNI=24 rats. (B) Animals after SNI surgery develop cold hypersensitivity from POD3 to POD56. *p<0.001, Kruskal-Wallis test with post hoc Dunn's tests. Naïve=9, sham=11, SNI=11 rats. 50% withdrawal threshold and cold scores are calculated as reported previously (Wang, et al. Anesthesiology 2011; 115: 812-821).

DETAILED DESCRIPTION OF THE INVENTION

Mood Disorders

Figure 4A:
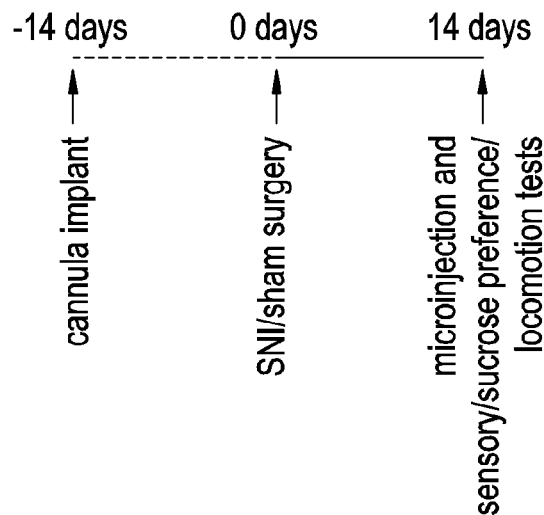
FIG. 4 shows that 2-pyrrolidinone, an AMPA potentiator that has been shown in vitro to specifically increase the currents of GluA2-lacking AMPA receptors (Nishizaki, et al., Brain Res Mol Brain Res 2002; 98: 130-134), can abolish pain-induced depression. When this compound was directly administered into the NAc (FIG. 4a, e), sensory hypersensitivity was unaltered (FIG. 4b, c). The depression-like behavior, however, was abolished, as shown by a return of sucrose preference to near control (painless) levels (FIG. 4d). These results suggest that CPARs, which are upregulated with the development of chronic pain, can be positively modulated further by AMPA potentiators to effectively reduce the depressive symptoms of pain. As NASPM has pro-depressant and 2-pyrrolidinone has antidepressant properties, we propose that CPARs in the NAc can bi-directionally regulate pain-induced depression.

Mood disorder is the term given for a group of diagnoses in the Diagnostic and Statistical Manual of Mental Disorders (DSM IV TR) classification system where a disturbance in the person's mood is hypothesized to be the main underlying feature. The classification is known as mood (affective) disorders in ICD 10. Two groups of mood disorders are broadly recognized; the division is based on whether the person has ever had a manic or hypomanic episode. Thus, there are depressive disorders, of which the best known and most researched is major depressive disorder (MDD) commonly called clinical depression or major depression, and bipolar disorder (BD), formerly known as "manic depression" and described by intermittent periods of manic and depressed episodes.

Depressive disorders include "Major depressive disorder (MDD)" commonly called major depression, unipolar depression, or clinical depression, where a person has two or more major depressive episodes. Depression without periods of mania is sometimes referred to as unipolar depression because the mood remains at one emotional state or "pole". Diagnosticians recognize several subtypes or course specifiers: Atypical depression (AD) is characterized by mood reactivity (paradoxical anhedonia) and positivity, significant weight gain or increased appetite ("comfort eating"), excessive sleep or somnolence (hypersomnia), a sensation of heaviness in limbs known as leaden paralysis, and significant social impairment as a consequence of hypersensitivity to perceived interpersonal rejection. Difficulties in measuring this subtype have led to questions of its validity and prevalence. Melancholic depression is characterized by a loss of pleasure (anhedonia) in most or all activities, a failure of reactivity to pleasurable stimuli, a quality of depressed mood more pronounced than that of grief or loss, a worsening of symptoms in the morning hours, early morning waking, psychomotor retardation, excessive weight loss (not to be confused with anorexia nervosa), or excessive guilt. Psychotic major depression (PMD), or simply psychotic depression, is the term for a major depressive episode, particularly of melancholic nature, where the patient experiences psychotic symptoms such as delusions or, less commonly, hallucinations. These are most commonly mood-congruent (content coincident with depressive themes). Catatonic depression is a rare and severe form of major depression involving disturbances of motor behavior and other symptoms. Here the person is mute and almost stuporose, and either immobile or exhibits purposeless or even bizarre movements. Catatonic symptoms also occur in schizophrenia, a manic episode, or be due to neuroleptic malignant syndrome. Postpartum depression (PPD) is listed as a course specifier in DSM-IV-TR; it refers to the intense, sustained and sometimes disabling depression experienced by women after giving birth. Postpartum depression, which has incidence rate of 10-15%, typically sets in within three months of labor, and lasts as long as three months. Seasonal affective disorder (SAD), also known as "winter depression" or "winter blues", is a specifier. Some people have a seasonal pattern, with depressive episodes coming on in the autumn or winter, and resolving in spring. The diagnosis is made if at least two episodes have occurred in colder months with none at other times over a two-year period or longer. Some such patients may display suicidal behavior.

Dysthymia is a chronic, different mood disturbance where a person reports a low mood almost daily over a span of at least two years. The symptoms are not as severe as those for major depression, although people with dysthymia are vulnerable to secondary episodes of major depression (sometimes referred to as double depression). Depressive Disorder Not Otherwise Specified (DD-NOS) is designated by the code 311 for depressive disorders that are impairing but do not fit any of the officially specified diagnoses. According to the DSM-IV, DD-NOS encompasses "any depressive disorder that does not meet the criteria for a specific disorder." It includes the research diagnoses of recurrent brief depression, and minor depressive disorder listed below. Recurrent brief depression (RBD), distinguished from major depressive disorder primarily by differences in duration. People with RBD have depressive episodes about once per month, with individual episodes lasting less than two weeks and typically less than 2-3 days. Diagnosis of RBD requires that the episodes occur over the span of at least one year and, in female patients, independently of the menstrual cycle.[1] People with clinical depression can develop RBD, and vice versa, and both illnesses have similar risks. Minor depressive disorder, or simply minor depression, refers to a depression that does not meet full criteria for major depression but in which at least two symptoms are present for two weeks.

Bipolar disorder (BD), a mood disorder formerly known as "manic depression" and described by alternating periods of mania and depression (and in some cases rapid cycling, mixed states, and psychotic symptoms). Subtypes include: Bipolar I is distinguished by the presence or history of one or more manic episodes or mixed episodes with or without major depressive episodes. A depressive episode is not required for the diagnosis of Bipolar I disorder, but depressive episodes are often part of the course of the illness. Cyclothymia is a different form of bipolar disorder, consisting of recurrent hypomanic and dysthymic episodes, but no full manic episodes or full major depressive episodes. Bipolar Disorder Not Otherwise Specified (BD-NOS), sometimes called "sub-threshold" bipolar, indicates that the patient suffers from some symptoms in the bipolar spectrum (e.g. manic and depressive symptoms) but does not fully qualify for any of the three formal bipolar DSM-IV diagnoses mentioned above. It is estimated that roughly one percent of the adult population suffers from bipolar I, roughly one percent of the adult population suffers from bipolar II or cyclothymia, and somewhere between two and five percent suffer from "sub-threshold" forms of bipolar disorder.

Substance-induced mood disorders refers to a mood disorder that can be classified as substance-induced if its etiology can be traced to the direct physiologic effects of a psychoactive drug or other chemical substance, or if the development of the mood disorder occurred contemporaneously with substance intoxication or withdrawal. Alternately, an individual may have a mood disorder coexisting with a substance abuse disorder. Substance-induced mood disorders can have features of a manic, hypomanic, mixed, or depressive episode. Most substances can induce a variety of mood disorders. For example, stimulants such as amphetamine (Adderall, Dexedrine; "Speed"), methamphetamine (Desoxyn; "Meth", "Crank", "Crystal", etc), and cocaine ("Coke", "Crack", etc) can cause manic, hypomanic, mixed, and depressive episodes. Alcohol-induced mood disorders include major depressive disorder occurring in heavy drinkers and those with alcoholism. Controversy has previously surrounded whether those who abused alcohol and developed depression were self-medicating their pre-existing depression, but recent research has concluded that, while this may be true in some cases, alcohol misuse directly causes the development of depression in a significant number of heavy drinkers. High rates of suicide also occur in those who have alcohol-related problems. It is usually possible to differentiate between alcohol-related depression and depression which is not related to alcohol intake by taking a careful history of the patient. Depression and other mental health problems associated with alcohol misuse may be due to distortion of brain chemistry, as they tend to improve on their own after a period of abstinence.

Benzodiazepine-induced mood disorders may be associated with long term use of benzodiazepines which have a similar effect on the brain as alcohol and are also associated with depression. Major depressive disorder can also develop as a result of chronic use of benzodiazepines or as part of a protracted withdrawal syndrome. Benzodiazepines are a class of medication commonly used to treat insomnia, anxiety and muscular spasms. As with alcohol, the effects of benzodiazepine on neurochemistry, such as decreased levels of serotonin and norepinephrine, are believed to be responsible for the increased depression. Major depressive disorder may also occur as part of the benzodiazepine withdrawal syndrome. In a long-term follow-up study of patients dependent on benzodiazepines, it was found that 10 people (20%) had taken drug overdoses while on chronic benzodiazepine medication despite only two people ever having had any pre-existing depressive disorder. A year after a gradual withdrawal program, no patients had taken any further overdoses. Depression resulting from withdrawal from benzodiazepines usually subsides after a few months but in some cases may persist for 6-12 months.

Chronic Pain and Postoperative Pain May Induce Depression

In patients who have chronic pain, depression is a common comorbidity. Postoperative pain is also known to cause depressed mood which may lead to prolonged recovery. Pain-induced depression has been studied in animal models as well in order to understand the molecular mechanisms involved so as to tailor the production of specific pharmacologic agents to treat this disease condition. It has been demonstrated that in rats, both chronic and postoperative pain lead to depression like behaviors (Wang et al, *Anesthesiology* 2011, 115: 812-821; Goncalves et al, *Experimental neurology* 2008, 213: 48-56; Hu et al, *Pain* 2009, 143: 206-212).

GluA1 Upregulation in the NAc Occurs with the Development of Chronic Pain.

Spared nerve injury (SNI) is a model for chronic pain as well as a model for severe postoperative pain (Decosterd, et al., *Pain* 2000; 87: 149-158) and induces both sensory hypersensitivity and depression like behaviors in rats (Wang, et al., *Anesthesiology* 2011; 115: 812-821). Here, this model is applied for neuropathic pain to study the role of APMA receptor signaling in the NAc. After the SNI surgery, rats experienced acute and chronic pain, as shown by increased hypersensitivity to mechanical and cold stimuli 3 and 14 days after the procedure (FIG. 1*a, b*) (Wang, et al., *Anesthesiology* 2011; 115: 812-821). Levels of GluA1 AMPA subunits from synaptoneurosome preparations of the NAc in SNI or sham-treated (control) rats were measured. A majority of the neurons in the NAc are medium spiny neurons (MSNs), and synaptoneurosome preparations reflect synaptic fractions of these neurons. No changes in GluA1 levels were seen 3 days after SNI, when pain remained relatively acute. However, 14 days after SNI, when pain is generally considered chronic (Decosterd, et al., *Pain* 2000; 87: 149-158), rats showed >50% increase in their synaptic GluA1 levels, relative to control (FIG. 1*c*). Thus, unlike most molecular changes in the brain that happen immediately after the onset of pain (Li, et al. *Science* 2010; 330: 1400-1404), GluA1 upregulation in the NAc occurs with the development of chronic pain after surgery, representing a unique form of plasticity. The level of GluA2 subunits, however, remained unchanged in the acute and chronic neuropathic pain states (FIG. 1*d*). This selective increase in GluA1 levels raises the possibility of formation of GluA2-lacking, calcium permeable AMPA receptors, which require GluA1 subunits (Liu, et al., *Trends Neurosci* 2007: 30: 126-134). The NAc contains core and shell regions. GluA1 levels are increased (by ~40%) in both regions after SNI (FIG. 1*e, f*). The core region has been proposed to play a larger role in cue-conditioned behavioral plasticity, whereas the shell region is thought to exert a greater influence in coding the value of aversive or appetitive stimulus (Sesack, et al., *Neuropsychopharmacology* 2010; 35: 27-47). These results show that chronic pain or postoperative pain causes molecular changes in both regions. The core region is particularly interesting, where pain may serve as a chronic cue to give rise to behavioral modification. In contrast, GluA1 levels are not altered after SNI in the hippocampus and cerebellum. GluA2 levels, meanwhile, are not significantly changed in either the core or shell region of NAc (FIG. 1e,f), nor the hippocampus or cerebellum.

No changes in the GluA1 levels in the whole cell fraction of the NAc after SNI treatment were observed. Thus, the increase in GluA1 subunits likely occurs locally at the synaptic sites. Increased synaptic GluA1 levels may be the result of increased exocytotic trafficking or localized synthesis, or decreased endocytosis or degradation. Phosphorylation of GluA1 Ser845 has been shown in vitro as a required step for GluA1 transport to the cell surface (Serulle, et al. *Neuron* 2007; 56: 670-688). Phospho-Ser845 was significantly increased (>50%) (FIG. 1g) in the synaptoneurosomes of the NAc; hence, this trafficking mechanism is conserved in the chronic or postoperative pain state. The ratio of pGluA1/total GluA1, however, was not altered after SNI (FIG. 1h). These results suggest that with chronic pain, GluA1 levels may be increased through either increased synthesis or decreased degradation, and that these GluA1 subunits are then phosphorylated at Ser845 to facilitate eventual synaptic targeting.

Functional CPARs are Formed at NAc Synapses in Response to Chronicor Postoperative Pain.

Phosphorylation at Ser845 suggests that GluA1 subunits are accumulated at the cell surface where they form functional receptors. A selective increase in GluA1 levels can lead to the formation of GluA2-lacking calcium permeable AMPA receptors with unique physiological properties (Liu, et al., *Trends Neurosci* 2007: 30: 126-134; Isaac, et al., *Neuron* 2007; 54: 859-871 and Cull-Candy, et al., *Curr Opin Neurobiol* 2006; 16: 288-297). Whole cell patch clamp slice recordings were performed in the NAc 14 days after the SNI to test this possibility. Excitatory postsynaptic currents (EPSCs) conducted by CPARs display two characteristics: inward rectification due to channel block at depolarized potentials by endogenous polyamines, and sensitivity to 1-naphthyl acetyl spermine (NASPM), a selective GluA2-lacking AMPA receptor blocker (Cull-Candy, et al., *Curr Opin Neurobiol* 2006; 16: 288-297). Medium spiny neurons were identified visually in the NAc core, and evoked EPSCs were recorded (FIG. 2i). When the current-voltage relationship of EPSCs was calculated (Conrad, et al., *Nature* 2008; 454: 118-121) (Supplementary Information), MSNs from SNI-treated animals displayed a significant increase in inward rectification compared with control neurons (FIG. 2a-d). In addition, bath application of NASPM reduced the amplitudes of EPSCs in neurons recorded from the SNI group, but not the control group (FIG. 2e-h). These results confirm biochemical findings of increased GluA1 levels and demonstrate that functional CPARs are specifically formed at NAc synapses in response to chronic pain.

CPARs, due to their high conductance, inward rectification, and permeability to $Ca^{2+}$, are well suited to regulate synaptic function and behavior Liu, et al., *Trends Neurosci* 2007: 30: 126-134; Conrad, et al., *Nature* 2008; 454: 118-121; Vikman, et al., *J Physiol* 2008; 586: 515-527; Clem, et al., *Science* 2010; 330: 1108-1112; Gu, et al., *Nature* 1996; 381: 793-796; Bellone, et al., *Nat Neurosci* 2011; 14: 1439-1446 and Argilli, et al., *J Neurosci* 2008; 28: 9092-9100). To explore the role of these receptors in the NAc, we injected NASPM directly into the NAc cores of SNI-treated rats (FIG. 3a, b). As previously reported (Wang, et al., *Anesthesiology* 2011; 115: 812-821), SNI induced both sensory and depressive characteristics of pain in rats. The sensory feature is shown by mechanical and cold hypersensitivity (FIG. 1a, b). The depressive feature of pain is shown by a decreased sucrose preference on the sucrose preference test, a test classically used to assess depression (FIG. 3f). We evaluated both sensory and depressive components of pain after NASPM treatment. NASPM did not alter mechanical or cold hypersensitivity after SNI (FIG. 3c, d), suggesting that while CPARs in the NAc are formed in response to chronic pain, they are not necessary for the sensory transmission of the pain signal. NASPM produced, however, a striking effect on the depression-like behavior of SNI-treated rats, as evidenced by a significant further decline in their already reduced sucrose preference (FIG. 3g). In contrast, sham-treated rats, lacking robust CPAR expression in their NAc (FIG. 2f, g), did not show this depression-like behavioral response to NASPM (FIG. 3h). Thus, while CPARs are not necessary for sensory pain transmission, they enable a novel modulation of the depression-like behavior induced by pain, through their regulation of synaptic function in the NAc. This finding is compatible with the general function of NAc in driving hedonic behaviors and their emerging role in depression (Nestler, et al., *Biol Psychiatry* 2006; 59: 1151-1159). At the systems level, the data indicate that not only is the affective circuit of pain distinct from the sensory pathway, but the NAc is a critical element in this affective circuit. The specificity of the observed behavioral phenotype is further supported by a lack of change in locomotion after NASPM treatment (FIG. 3e).

Figure 4B:
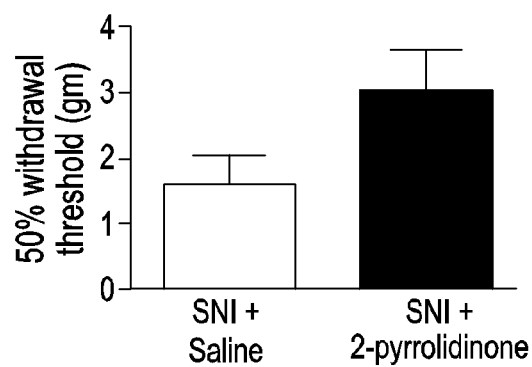
Figure 4C:
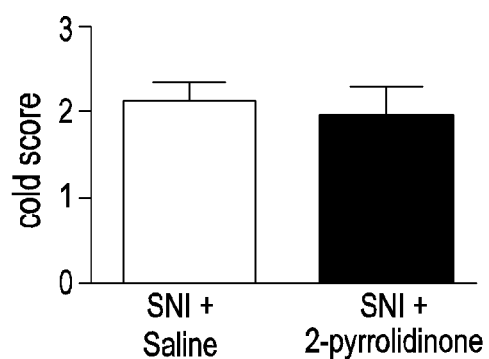
Figure 4D:
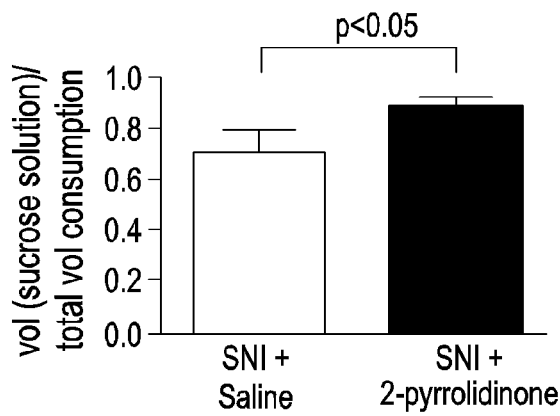
Figure 4E:
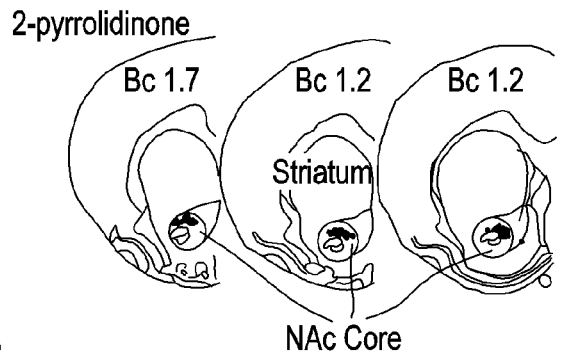

If CPARs protect against pain-induced depression, it is likely a native adaptive mechanism. Pharmacologically enhancing this mechanism could further alleviate the depressive symptoms of pain. AMPA potentiators are a class of compounds that increase AMPA receptor currents by slowing deactivation of open channels (Lynch, et al., *Trends Neurosci* 2006; 29: 554-562; Jin, et al., *J Neurosci* 2005; 25: 9027-9036). This activity dependent feature would synergize with the dynamic formation of functional CPARs that occur specifically in the chronic pain state to produce greater antidepressant efficacy. 2-pyrrolidinone is an AMPA potentiator that has been shown in vitro to specifically increase the currents of GluA2-lacking AMPA receptors (Nishizaki, et al., *Brain Res Mol Brain Res* 2002; 98: 130-134). When this compound was directly administered into the NAc (FIG. 4a, e), sensory hypersensitivity was unaltered (FIG. 4b, c). The depression-like behavior, however, was abolished, as shown by a return of sucrose preference to near control (painless) levels (FIG. 4d). These results suggest that CPARs, which are upregulated with the development of chronic pain, can be positively modulated further by AMPA potentiators to effectively reduce the depressive symptoms of pain. As NASPM has pro-depressant and 2-pyrrolidinone has anti-depressant properties, we propose that CPARs in the NAc can bi-directionally regulate pain-induced depression.

The NAc Forms a Key Link Between Pain and Depression.

The findings described herein expand our understanding of the nucleus accumbens as an important brain region for processing aversive stimuli (Becerra, et al., *Eur J Pain* 2008; 12: 866-869; Geha, et al. *Neuron* 2008; 60: 570-581; Gear, et al., *Journal of Neuroscience* 1999; 19: 7175-7181 and Roitman, et al., *Neuron* 2005; 45: 587-597). They demonstrate that the NAc forms a key link between pain and depression. In patients with chronic pain, grey matter atrophy has been found in the NAc (Geha, et al. *Neuron* 2008; 60: 570-581), suggesting a decrease in the overall neuronal activities in the NAc. The behavioral relevance of such a decrease has not been tested. We show here that increased neural transmission in the NAc through CPAR activation decreases depression, whereas reducing the NAc transmission by blocking CPARs has the opposite effect. Thus, our data suggest that decreased neuronal activities in the NAc observed in the chronic pain patients likely contribute to their depressive symptoms of pain. This decrease in neuronal activities in the NAc (Geha, et al. *Neuron* 2008; 60: 570-581) may also explain why, despite the formation of CPARs, rats in our study still show depression-like behaviors after SNI, lending support to the idea that CPARs are formed as an adaptive mechanism.

The molecular mechanisms for pain-induced depression remain elusive. Glutamate signaling in the NAc plays a key role in this process. Ketamine, like AMPA potentiators, can effectively treat pain-induced depression without exerting long lasting sensory pain relief (Wang, et al., *Anesthesiology* 2011; 115: 812-821 Ketamine has also been shown to increase GluA1 levels (Li, et al. *Science* 2010; 329: 959-964). Thus, both ketamine-induced and endogenous increases in GluA1 expression are capable of providing antidepressant activities in the chronic pain state. Endogenously, the formation of CPARs in the NAc may be an important adaptive response to promote antidepressant effects in the presence of chronic aversive stimuli. The establishment of CPARs in the NAc may provide similar antidepressant effects in other models of depression.

Depression is an Important Feature of the Affective Pain Experience.

Depression is an important feature of the affective pain experience, and pain-induced depression decreases analgesic efficacy and further impairs daily function. A key node in the affective pain circuit is the NAc. At the synaptic level, calcium permeable AMPA receptors are formed in the NAc to protect against depression induced by chronic neuropathic pain, and AMPA potentiators can further enhance this protective function. These data demonstrate circuit and synaptic elements for understanding the relationship between pain and depression. These data also demonstrate that CPARs are a novel therapeutic target for treating the depressive symptoms of chronic pain.

Assays for Selecting and Therapeutic Agents

The present invention also includes assays for selecting for a suspected therapeutic agent for possible use in the treatment of a mood disorder such as depression associated with, concurrent with or subsequent to pain, e.g. chronic pain or postoperative pain. One such method for selecting a suspected therapeutic agent for possible use in the treatment of a mood disorder such as depression associated with, concurrent with or subsequent to pain, e.g. chronic pain or postoperative pain comprises administering a potential therapeutic agent to a mammal such as a human.

The present invention also provides the agents obtained by such methods. The agent may be, for instance, a small organic molecule. These and other aspects of the present invention will be better appreciated by reference to the following drawings and Detailed Description. In a specific embodiment, the term "about" means within 20%, preferably within 10%, and more preferably within 5%.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Definitions

As used herein, the following terms are defined as follows:

As used herein a "small organic molecule" is an organic compound [or organic compound complexed with an inorganic compound (e.g., metal)] that has a molecular weight of less than 3 kilodaltons, and preferably less than 1.5 kilodaltons. An "agent" of the present invention is preferably a small organic molecule.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Two amino acid sequences are "substantially homologous" when at least about 70% of the amino acid residues, preferably at least about 80%, and most preferably at least about 90, 91, 92, 93, 94, 95, 96, 97, 98, or 99% of the amino acid residues are identical, or represent conservative substitutions.

Analogs and derivatives of a protein are normally said to be substantially homologous.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The terms "a fragment, derivative or analog thereof" refer in some instances to amino acid sequences, peptides and proteins having about 50%, 60%, 70%, 75%, 80%, 85%, 90%, 95%, 96%, 97%, 98%, 99% or about 100% identical sequence to the naturally occurring wild type Mov10 protein, such as, for instance, the Mov10 protein sequence provided in SEQ ID NO:1.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense or stimulates a response that would be elicited on binding of a natural ligand to a binding site.

The terms "inhibitor" or "antagonist" refers in some instances to a ligand that stimulates the receptor the ligand binds to in the broadest sense or stimulates a response that would be elicited on binding of a natural ligand to a binding site in instances where the response that is elicited results in reducing or inhibiting the biological activity of its target. The terms "inhibitor" or "antagonist" are intended to encompass agents or molecules that reduce or inhibit the biological activity of another target molecule such as a protein. Such agents or molecules may function by binding to a target molecule such as a protein or may function by reducing the amount of the target molecule such as a protein that is transcribed, translated or expressed. Such agents may be, for instance, small molecules, antibodies or nucleic acids such as, for instance, siRNA, iRNA, etc.

The term 'assay' means any process used to measure a specific property of a compound or agent. A 'screening assay' means a process used to characterize or select compounds based upon their activity from a collection of compounds.

"Preventing" or "prevention" refers to a reduction in risk of acquiring a disease or disorder such as depression or symptoms thereof.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

Administration of Therapeutic Compositions

According to the present invention, the component or components of a therapeutic composition of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In some instances, the components or composition are administered to and are introduced by injection into the blood. In another embodiment, the therapeutic components or composition can be delivered in a vesicle, in particular a liposome (See, Langer, Science 249:1527-1533 (1990); Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the therapeutic compound can be delivered in a controlled release system. For example, an antibody may be administered using intravenous infusion, an implantable osmotic pump, a transdermal patch, liposomes, or other modes of administration. In one embodiment, a pump may be used (See, Langer, supra; Sefton, CRC Crit. Ref Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of a therapeutic target, e.g., the brain, thus requiring only a fraction of the systemic dose (See, e.g., Goodson, in Medical Applications of Controlled Release, supra, vol. 2, pp. 115-138 (1984)). Other controlled release systems are discussed in the review by Langer, Science 249:1527-1533 (1990).

Thus, a therapeutic composition of the present invention can be delivered by intravenous, intraarterial, intraperitoneal, intramuscular, or subcutaneous routes of administration. Alternatively, the therapeutic composition, properly formulated, can be administered by nasal or oral administration. A constant supply of the therapeutic composition can be ensured by providing a therapeutically effective dose (i.e., a dose effective to induce metabolic changes in a subject) at the necessary intervals, e.g., daily, every 12 hours, etc. These parameters will depend on the severity of the disease or condition being treated, other actions, such as diet modification, that are implemented, the weight, age, and sex of the subject, and other criteria, which can be readily determined according to standard good medical practice by those of skill in the art. A subject in whom administration of the therapeutic composition is an effective therapeutic regiment for is preferably a human, but can be a primate with a related condition. Thus, as can be readily appreciated by one of ordinary skill in the art, the methods and pharmaceutical compositions of the present invention are particularly suited to administration to a number of animal subjects including humans.

Transgenic Vectors and Effecting Expression

In one embodiment, a gene encoding a therapeutic compound can be introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus macrophage can be specifically targeted. Examples of particular vectors include, but are not limited to, an attenuated adenovirus vector, such as the vector described by Stratford-Perricaudet et al. *J. Clin. Invest.* 90:626-630 (1992)), and a defective adeno-associated virus vector (Samulski et al., *J. Virol.* 61:3096-3101 (1987); Samulski et al., *J. Virol.* 63:3822-3828 (1989)).

In another embodiment the gene or antigene or RNA can be introduced in a retroviral vector, e.g., as described in Anderson et al., U.S. Pat. No. 5,399,346; Mann et al., 1983, *Cell* 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; International Patent Publication No. WO 95/07358, published Mar. 16, 1995, by Dougherty et al.; and Kuo et al., 1993, *Blood* 82:845. Targeted gene delivery is described in International Patent Publication WO 95/28494, published October 1995.

Alternatively, the vector can be introduced in vivo by lipofection (Feigner, et. al., *Proc. Natl. Acad. Sci. U.S.A.* 84:7413-7417 (1987); see Mackey, et al., *Proc. Natl. Acad. Sci. U.S.A.* 85:8027-8031 (1988); Feigner and Ringold, *Science* 337:387-388 (1989)). Lipids may be chemically coupled to other molecules for the purpose of targeting (See, Mackey, et. al., supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (See, e.g., Wu et al., *J. Biol. Chem.* 267:963-967 (1992); Wu and Wu, *J. Biol. Chem.* 263:14621-14624 (1988); Hartmut et al., Canadian Patent Application No. 2,012,311, filed Mar. 15, 1990).

Maniatis et al., supra; DNA Cloning, Vols. I & II, supra; Nucleic Acid Hybridization, supra.

Methods for Screening Drug Libraries

Any screening technique known in the art can be used to screen for agents that affect GluA1 or CPARs. The present invention contemplates screens for small molecule ligands or ligand analogs and mimics, as well as screens for natural ligands that bind to or agonize such activity in vivo. For example, natural products libraries can be screened using assays of the invention for molecules that increase CPAR expression, concentration, or biological activity or potentiating a CPAR current. Identification and screening of such agents is further facilitated by determining structural features of the protein, e.g., using X-ray crystallography, neutron diffraction, nuclear magnetic resonance spectrometry, and other techniques for structure determination. These techniques provide for the rational design or identification of such agents.

Another approach uses recombinant bacteriophage to produce large libraries. Using the "phage method" (Scott and Smith, 1990, *Science* 249:386-390 (1990); Cwirla, et al., *Proc. Natl. Acad. Sci.*, 87:6378-6382 (1990); Devlin et al., *Science*, 249:404-406 (1990)), very large libraries can be constructed. A second approach uses primarily chemical methods, of which the Geysen method (Geysen et al., *Molecular Immunology* 23:709-715 (1986); Geysen et al. *J. Immunologic Method* 102:259-274 (1987)) and the method of Fodor et al. *Science* 251:767-773 (1991)) are examples. Furka et al. 14th International Congress of Biochemistry, Volume 5, Abstract FR:013 (1988); Furka, *Int. J. Peptide Protein Res.* 37:487-493 (1991)), Houghton (U.S. Pat. No. 4,631,211, issued December 1986) and Rutter et al. U.S. Pat. No. 5,010,175, issued Apr. 23, 1991 describe methods to produce a mixture of peptides that can be tested as agonists or antagonists.

In another aspect, synthetic libraries (Needels et al., *Proc. Natl. Acad. Sci.* USA 90:10700-4 (1993); Ohlmeyer et al., *Proc. Natl. Acad. Sci.* USA 90:10922-10926 (1993); Lam et al., International Patent Publication No. WO 92/00252; Kocis et al., International Patent Publication No. WO 9428028, each of which is incorporated herein by reference in its entirety), and the like can be used to screen for agents according to the present invention.

The screening can be performed with recombinant cells that express CPARs, or alternatively, using purified protein, e.g., produced recombinantly. For example, the ability of a labeled, soluble or solubilized that includes the ligand-binding portion of the molecule, to bind ligand can be used to screen libraries, as described in the references cited above. In addition, orphan chemokines, potential chemokines, or potential ligands that are obtained from random phage libraries or chemical libraries, as described herein, can be tested by any of the numerous assays well known in the art and exemplified herein. In one particular embodiment of the present invention, an in situ assay is employed in which the detection of the calcium signaling elicited by the binding of a potential chemokine to a chemokine receptor is indicative of the chemokine having specificity for the chemokine receptor, and therefore is a ligand.

Transgenic Vectors and Inhibition of Expression

In one embodiment, a gene encoding GluA1, or antisense or ribozyme specific for GluA1 mRNA (termed herein an "antigen") or a reporter gene can be introduced in vivo in a viral vector. Alternatively, a RNA (coding or noncoding) which can regulate the translation of GluA1 may be introduced in similar manner. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus macrophage can be specifically targeted. Examples of particular vectors include, but are not limited to, a defective herpes virus 1 (HSV1) vector [Kaplitt et al., *Molec. Cell. Neurosci.* 2:320-330 (1991)], an attenuated adenovirus vector, such as the vector described by Stratford-Perricaudet et al. *J. Clin. Invest.* 90:626-630 (1992), and a defective adeno-associated virus vector (Samulski et al., *J. Virol.* 61:3096-3101 (1987); Samulski et al., *J. Virol.* 63:3822-3828 (1989)).

In another embodiment the gene or antigene or RNA can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; International Patent Publication No. WO 95/07358, published Mar. 16, 1995, by Dougherty et al.; and Kuo et al., 1993, *Blood* 82:845. Targeted gene delivery is described in International Patent Publication WO 95/28494, published October 1995.

Alternatively, the vector can be introduced in vivo by lipofection (Felgner, et. al., *Proc. Natl. Acad. Sci. U.S.A.* 84:7413-7417 (1987); see Mackey, et al., *Proc. Natl. Acad. Sci. U.S.A.* 85:8027-8031 (1988); Felgner and Ringold, *Science* 337:387-388 (1989)]. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., *J. Biol. Chem.* 267:963-967 (1992); Wu and Wu, *J. Biol. Chem.* 263:14621-14624 (1988); Hartmut et al., Canadian Patent Application No. 2,012,311, filed Mar. 15, 1990).

DETAILED DESCRIPTION OF THE PREFERRED EMBODIMENTS

Example 1

Using the spared nerve injury (SNI) model in rats, GluA1 expression will be shown to be increased at synapses in postoperative pain states. As GluA1 subunits can form CPARs, electrophysiology recordings may be used to determine active CPAR currents. We will determine increases in GluA1 levels at the synapses of NAc neurons and define the time course of this upregulation in spared nerve injury (SNI) model, by examining GluA1 levels in synaptosome, post-synaptic density (PSD) and cell surface fractions and by examining phosphorylation of Ser845, using Western blots.

Postoperative pain elevates GluA1 subunit levels at synapses of NAc neurons, a process mediated though Ser845 phosphorylation. Similar to rewarding stimuli such as cocaine, pain also activates the NAc (Gear, et al *J. Neurosci* 1999; 19: 7175-81; Volkow, et al., *Arch Neurol* 2007; 64: 1575-9; Wise, *Nat Rev Neurosci* 2004; 5: 483-94; and Brischoux, et al., *Proc Natl Acad Sci USA* 2009; 106: 4894-9). Thus, it is not surprising for key glutamate signaling mechanisms such as increased expression of GluA1 subunits of AMPA receptors to be conserved. Increased GluA1 levels leading to the formation of CPARs have been shown in the medium spiny neurons (MSNs) of the NAc in the presence of rewards (Conrad, et al., *Nature* 2008; 454: 118-21). Preliminary work has demonstrated such an increase. We will identify the time course for GluA1 upregulation in the postoperative period, which will allow future mechanistic studies to examine the initiation and maintenance of GluA1 expression. We will also test the mechanism of Ser845 phosphorylation in GluA1 trafficking in the NAc. Phosphorylation of Ser845 is required to target GluA1 to the cell surface in in vitro studies (Ehlers, et al., *Neuron* 2007; 54: 447-60; He, et al *Natl Acad Sci USA* 2009; 106: 20033-8) and in in vivo studies on food restricted rats (Carr, et al., *Neuroscience* 2010; 165: 1074-86). Anatomically, the NAc contains core and shell subregions that are thought to be functionally distinct. Both regions are implicated in mood regulation (Nestler, et al., *Biol Psychiatry* 2006; 59: 1151-9).

Figure 6A:
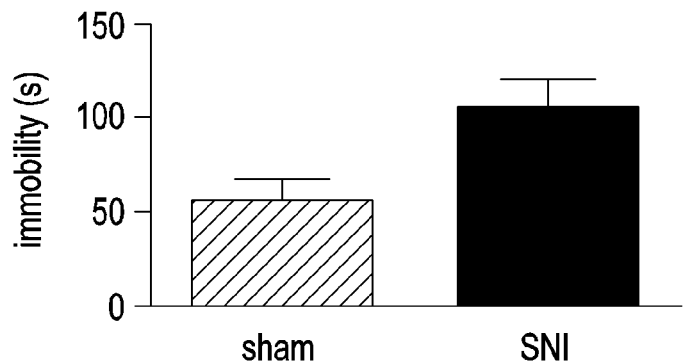
FIG. 6 represents that acute and chronic pain cause depression-like behavior. (A) SNI increases immobility on the forced swim test. *p<0.05, student's t test. n=6 in each group. (B) SNI group shows chronic decreases in sucrose preference. ***p<0.001, *P<0.05, two-way ANOVA with post-hoc Bonferroni tests. Sham=13, SNI=17. (C) SNI and sham cause initial decreases of sucrose preference. Sham group recovers on POD 7. *P<0.05. NS: non-significant. Naïve=17, sham=17, SNI=19.
Figure 6B:
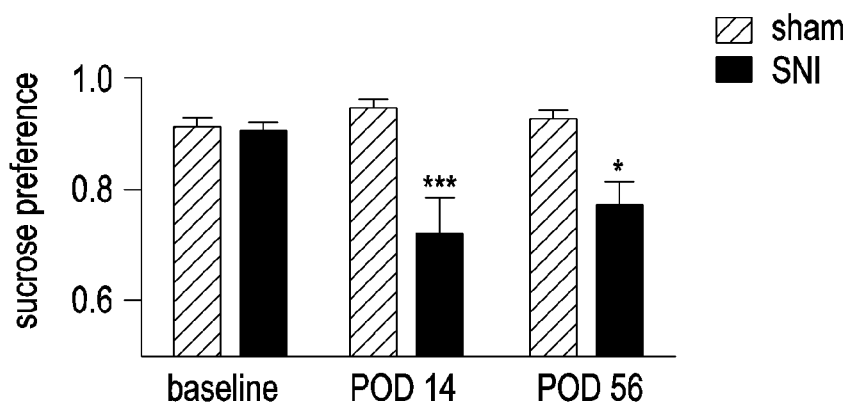
Figure 6C:
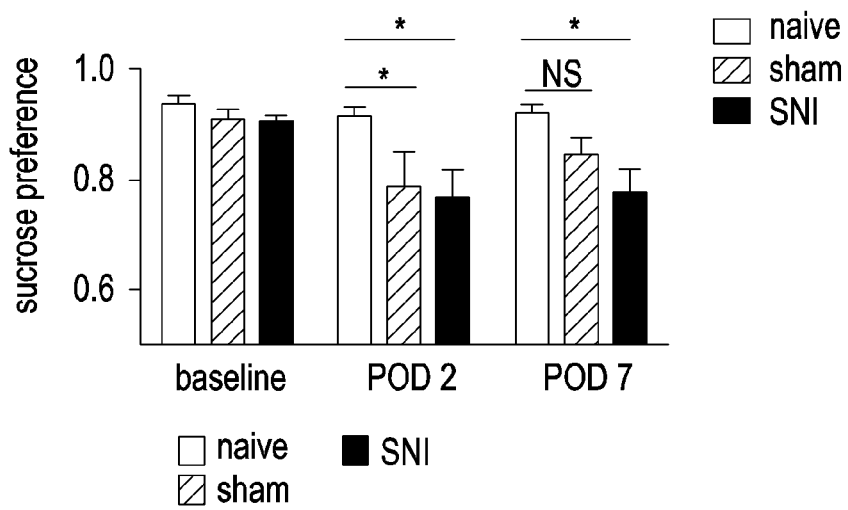
Figure 7A:
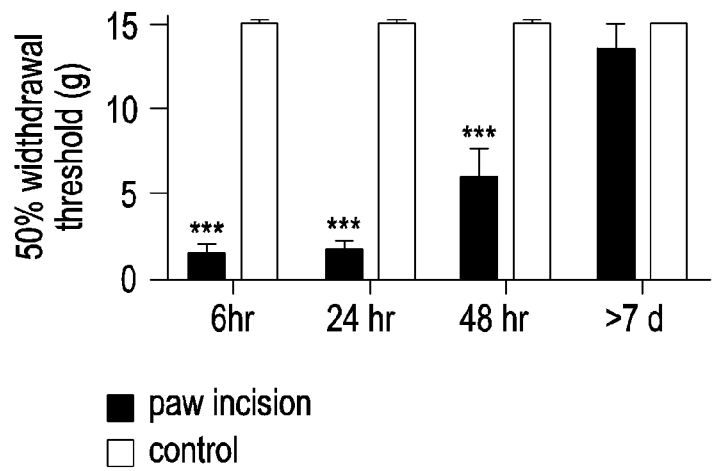
FIG. 7 depicts that paw incision (PI), which mimics acute postoperative, also induces reversible sensory hypersensitivity and depressive symptoms. (A) Rats develop reversible mechanical hypersensitivity after paw incision. ***p<0.001, two-way ANOVA, with post-hoc Bonferroni tests. n=12 in both PI and control groups. (B) PI induces transient depression-like behavior. *p<0.05, n=12.
Figure 7B:
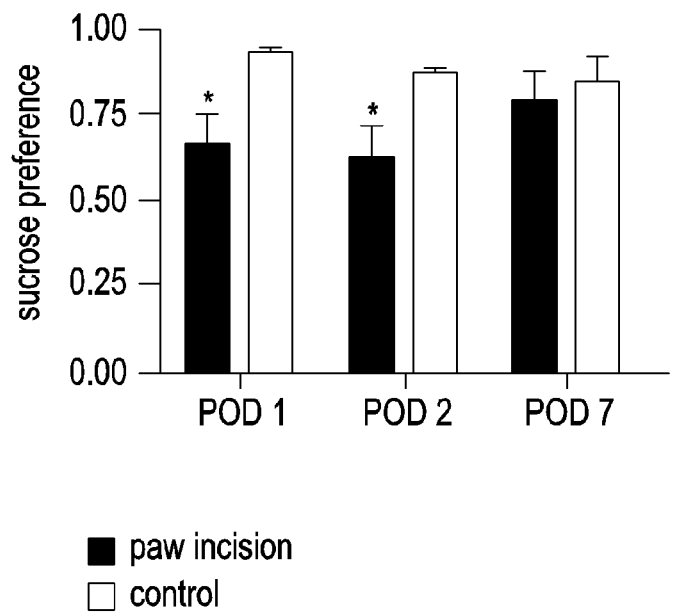
Figure 8A:
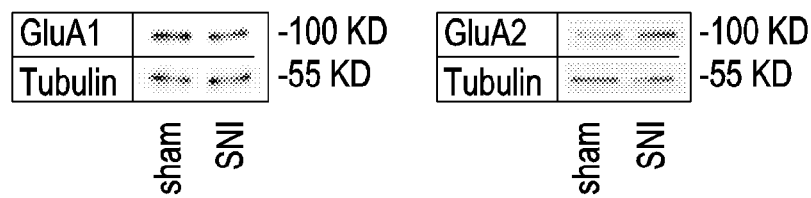
FIG. 8 demonstrates that neither GluA1 or GluA2 level is elevated in hippocampus or cerebellum regions of the brain. Thus, the upregulation of GluA1 observed in the NAc is likely highly specific.
Figure 8B:
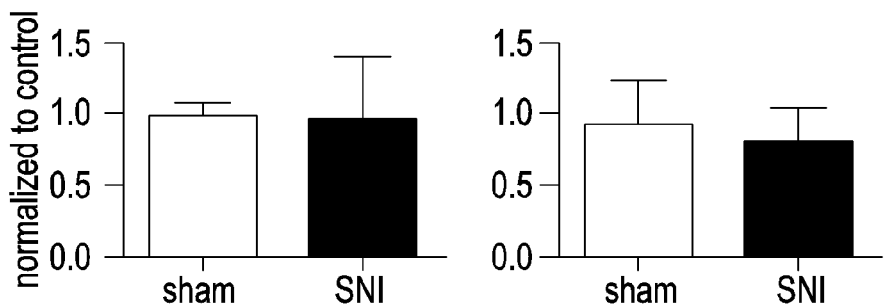
Figure 8C:
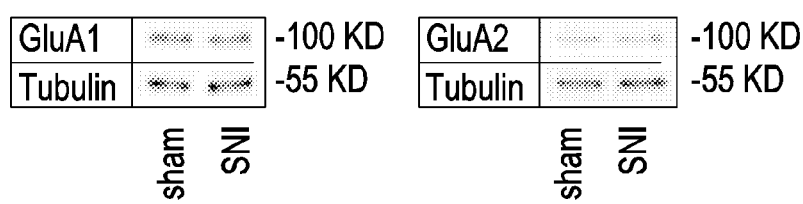
Figure 8D:
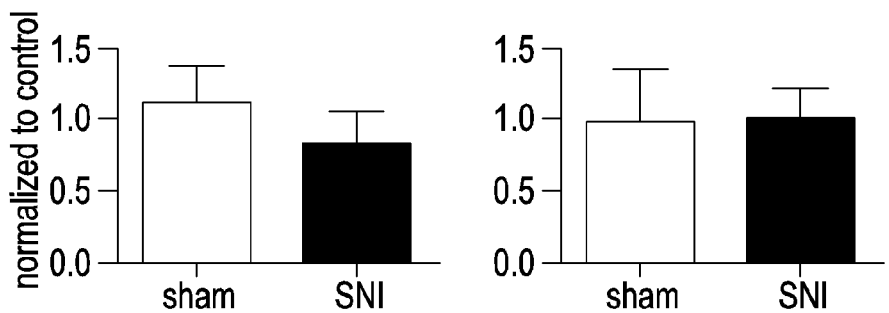

After SNI, rats develop sensory hypersensitivity, as measured by increased withdrawal response to von Frey filaments (mechanical allodynia) and acetone (cold allodynia) (FIG. 5) (Wang, et al. *Anesthesiology* 2011; 115: 812-821). The sucrose preference test (SPT) and forced swim test (FST) are used to assess depression. Preference for sucrose over water is a normal hedonic response in rats, whereas a decreased sucrose preference on the SPT represents anhedonia, a typical feature of depression. On the FST, increased time of immobility, rather than swimming, suggests behavioral despair, another feature of depression. SNI-treated rats show persistently increased immobility (on FST) and decreased sucrose preference (on SPT), suggesting chronic postoperative depression concurrent with sensory pain symptoms (FIG. 6). Sham-operated rats only develop depression-like behavior in the immediate postoperative period (FIG. 6C), due to acute incisional pain. These experiments were repeated in the PI model, and sensory and depressive symptoms both develop within 24 hours after paw incision and resolve 7 days later (FIG. 7). Thus, in animal models both acute and chronic postoperative pain cause depressive behavior. Hence, SNI and PI are valid preclinical models to test the regulation of the depressive symptoms of postoperative pain.

Example 2

SNI Model Displays Increased GluA1 Expression

Western blots were used to compare GluA1 levels in pain and control groups. On POD 14, SNI-treated rats, compared with control, show a statistically significant increase in GluA1 levels in the synaptosomes of their MSNs (FIG. 1C). In contrast, GluA2 levels do not change (FIG. 1D). Synaptosomes are biochemical preparations that isolate the synaptic membrane and proteins and are commonly used to study AMPA receptor trafficking at the synapse. An increase of synaptic GluA1 expression without a concurrent change in the GluA2 level evidences the formation of GluA2-lacking, calcium permeable AMPA receptors (CPARs). We will test functional CPAR currents.

Pain may induce depression, and depression, rather than pain, then increases GluA1 expression. However, this is unlikely, because other models for depression, such as chronic mild stress model, cause either unchanged or decreased GluA1 levels (Toth, et al., *J. Neurochem* 2008; 107: 522-32).

Example 3

Demonstrate Increased GluA1 Levels at Synaptic Sites

Following synaptosome preparations, Western blots will be used to confirm increased GluA1 levels in the SNI model. Synaptosomes contain both pre- and postsynaptic regions. Because AMPA receptors are mostly found at the postsynaptic site, synaptosomes are commonly used to study AMPA receptors. To test the time course of synaptic GluA1 expression, synaptosomes at various postoperative time points will be prepared, followed by Western blot analysis to compare GluA1 and GluA2 levels between pain and control groups in both SNI and PI models.

Test the Role of Phosphorylation of Ser845 in GluA1 Surface Expression.

Ser845 phosphorylation is a key step for GluA1 surface transport (He, et al *Natl Acad Sci USA* 2009; 106: 20033-8). Whether this mechanism is conserved in postoperative pain will be determined by repeating the above experiments in synaptosomes using an antibody specific for pSer845. This will provide mechanistic insights into the regulation of GluA1 trafficking in postoperative pain, as we plan to correlate the timeframe of Ser845 phosphorylation with GluA1 surface expression.

Identify the Regional Specificity for GluA1 Trafficking.

The above biochemical experiments will be repeated with distinct core and shell regions of the NAc. Furthermore, to verify that findings for GluA1 synaptic expression are specific to the NAc, we will repeat the above experiments using tissues from dorsal striatum, hippocampus and cerebellum as controls.

Experimental Design

1) Chronic Postoperative Pain Model

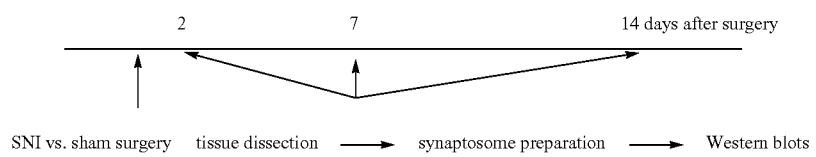

2) Acute Postoperative Pain Model

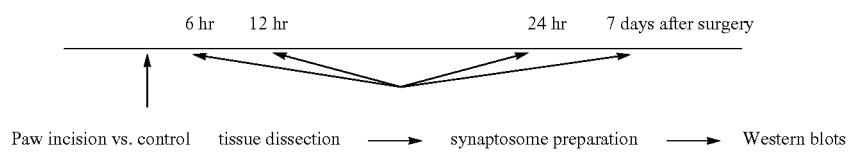

Power Analysis.

Based on preliminary data, there will be an average of about 50% increase in GluA1 levels on the western blot in pain groups relative to control, with an average standard deviation (STD) of about 40%. Power analysis yields n=10 rats in both pain and control groups to reach $p<0.05$ for each biochemical assay.

Results.

Time Course of GluA1 Elevation in the SNI Model.

Preliminary data established increased GluA1 levels without changes in GluA2 levels 14 days after SNI in synaptosome and surface fractions, and there will be similar findings in the PSD fraction as well. In terms of the time course, on postoperative day (POD) 2, both SNI and sham groups have acute pain (FIGS. 5-6), and there may be no difference in their GluA1 levels. On POD7, the sham group no longer experiences incisional pain, but the SNI group experiences neuropathic pain, and thus the SNI group should express higher levels of GluA1.

Time Course of GluA1 Elevation in the PI Model.

We will measure GluA1 levels in synaptosomes at various time points after paw incision. Earlier time points such as 6 and 12 hr after PI help to define the onset of GluA1 upregulation. The most interesting time point will be POD 7, when PI-induced acute pain is resolved (FIG. 7). If GluA1 levels in the PI group return to control levels on POD 7, this would suggest that pain initiates and maintains GluA1 expression; continued GluA1 elevation, however, suggests that pain initiates but is not required to maintain GluA1 expression. It is also possible that, GluA1 levels do not increase until POD 7, suggesting that GluA1 upregulation is a delayed response to pain. Hence, this time course study will lead to future mechanistic investigations on the initiation and maintenance of synaptic GluA1 expression.

A chronic inflammatory pain model will also be used. Complete Freund's Adjuvant (CFA) or saline (control) will be injected into the paws of rats and test GluA1 levels 7 days later. If GluA1 levels are elevated in the CFA model, GluA1 signaling is likely a property of chronic pain. If CFA fails to elicit a GluA1 increase, GluA1 upregulation may be an exclusive property of neuropathic pain. Chronic and especially chronic neuropathic pain is refractory to current treatments, and these results may offer new mechanistic insights and therapeutic options. An established CFA model has been established (Weyerbacher, et al., *Pain* 2010; 148: 237-46).

Phophorylation at Ser845.

Ser845 phosphorylation is a key step for GluA1 surface transport. Ser845 phosphorylation will coincide with or precede GluA1 surface expression in postoperative pain. Ser845 can be phosphorylated by either cAMP-dependent protein kinase A (PKA) (Esteban, et al., *Nat Neurosci*, 2003; 6: 136-43) or cGMP-dependent protein kinase II (cGKII) (Serulle, et al., *Neuron* 2007; 56: 670-88), and the PKA pathway can be initiated by dopamine signaling (Sun, et al., *J Neurosci* 2005; 25: 7342-51). Study on Ser845 phosphorylation may lead to future studies on the upstream signals that initiate and maintain GluA1 surface trafficking in the pain state, including possible interactions between glutamate and dopamine signals. The role of other phosphorylation sites may be examined. Ser818 phosphorylation by protein kinase C (PKC) and Ser831 phosphorylation by either PKC or $Ca^{2+}$/calmodulin-dependent protein kinases II (CaMKII) are both important for the synaptic incorporation of GluA1 (Esteban, et al., *Nat Neurosci,* 2003; 6: 136-43; Semite, et al., *Neuron* 2007; 56: 670-88; Boehm, et al., *Neuron,* 2006; 51: 213-25). We have shown that indeed, pSer845 levels are elevated in rats that have chronic pain (FIG. 1G). The ratio of pSer845/total GluA1 is not altered (FIG. 1H), however, suggesting that while trafficking mechanism is conserved in the chronic pain state, trafficking alone cannot account for the increase in GluA1 levels. More likely, GluA1 levels are increased in the pain state by increased synthesis or decreased degradation, and these GluA1 subunits are then transported to the synaptic surface.

Regional Specificity of GluA1 Upregulation.

GluA1 elevation has been described in the core region of the NAc from studies on cocaine (Conrad et al., *Nature* 2008; 454: 118-21; Bachtell, et al., *Eur J Neurosci* 2008; 27: 2229-40), and there will be a similar increase in the present study. GluA1 may also be increased in the shell region. There will be no changes in GluA1 levels in dorsal striatum and cerebellum which are not known to respond to pain. However, there may be an increase in GluA1 levels in the hippocampus, which has been shown to respond to pain (Duric et al., *Mol Pain* 2007; 3: 32). Elevated hippocampal GluA1 levels would suggest a general rather than regionally restricted role for CPARs in postoperative pain states. We showed that in both core and shell subregions, synaptic GluA1 levels are elevated, whereas GluA2 levels remain unchanged (FIG. 1E, F). In addition, GluA1 levels are not elevated in either the hippocampus or the cerebellum (FIG. 8), arguing that the GluA1 upregulation that we observe is specific to the NAc.

Example 4

Postoperative Pain Leads to the Formation of CPARs, Using Whole Cell Patch Clamp Recordings in NAc Slices from SNI and PI Models Increased GluA1 expression in the NAc leads to the formation of GluA2-lacking calcium permeable AMPA receptors in both acute and chronic pain models. In preliminary biochemical studies, a selective upregulation of GluA1 at synapses with no changes in GluA2 levels (FIG. 4) was demonstrated. The NAc primarily express GluA1 and GluA2 subunits, and in cocaine studies (Conrad et al., *Nature* 2008; 454: 118-21), selective increases in GluA1 subunits lead to the formation of GluA2-lacking calcium permeable AMPA receptors (CPARs) with unique physiologic properties including higher conductance, inward rectification and calcium permeability, all of which contribute to augmentation of synaptic transmission and facilitating synaptic plasticity (Greger, et al *Trends Neurosci* 2007; 30: 407-16; Liu, et al., *Trends Neurosci* 2007; 30: 126-34). Formation of CPARs in postoperative pain will be examined using electrophysiology.

AMPA receptors conduct excitatory postsynaptic currents (EPSCs), which represent synaptic responses through AMPA receptors elicited by local electrical stimulation. A key feature of EPSCs conducted by CPARs is their inward rectification due to channel blockade at depolarized potentials by endogenous polyamines. In acute coronal slices containing the NAc, we measured EPSCs from MSNs in the core region of the NAc to construct current-voltage (I-V) relationships. The rectification indices for MSNs from animals treated with sham or SNI procedure on POD 14 were examined. Rectification index $(i_r)=[I_{-70}/(70-E_{rev})]/[I_{+40}/(40-E_{rev})]$ ($E_{rev}$: reversal potential, $I_{-70}$, $I_{+40}$: EPSCs at $-70$ mV and $+40$ mV). Preliminary data showed a statistically significant increase in the rectification index of neurons in the SNI group compared with those in the sham group (FIG. 5). Because inward rectification is a hallmark of CPAR currents, these data are highly suggestive of the presence of functional CPARs in animals with chronic postoperative pain.

Methods.

In addition to inward rectification, another feature of CPAR currents is that at negative voltages they can be blocked by 1-naphthyl acetyl spermine (NASPM), a synthetic polyamine that is highly specific for CPARs with minimal effects on calcium impermeable AMPA receptor and other glutamate receptors (Conrad, et al., *Nature* 2008; 454: 118-21; Clem, et al., *Science* 2010; 330: 1108-12). Acute coronal slices containing the NAc will be prepared and individual medium spiny neurons identified by their characteristic shapes under microscopy. While the NAc has both core and shell regions, CPARs have been recorded in the core under conditions of rewards (Conrad, et al., *Nature* 2008; 454: 118-21), and preliminary data also suggest the presence of CPARs in the NAc core region. Whole cell patch (voltage) clamp recordings will be performed, however, from both regions. In the presence of picrotoxin and APV (to block γ-aminobutyric Acid—GABA and N-Methyl-D-aspartic acid—NMDA—currents), evoked EPSCs will be measured and an I-V relationship constructed, in pain and control groups of both SNI and PI models. After baseline recordings, NASPM (200 µM) will be perfused, and EPSCs measured, as described previously (Conrad, et al., *Nature* 2008; 454: 118-21). The amplitudes of EPSCs will be compared in the presence and absence of NASPM or saline (control). These experiments will be done at time points when GluA1 upregulation is established by biochemical assays. To verify the effects of NASPM, another blocker, IEM 1460 which is an agonist for polyamines and blocks CPARs and, to a lesser degree, NMDA receptors (Fortin, et al, *J Neurosci* 2010; 30: 11565-75; Magazanik, et al., *J Physiol* 1997; 505 (Pt 3): 655-63) will be used. A difference of 0.6 on the rectification index between the pain and control group, with a STD of 0.35. Power analysis yields n=7 neurons in each group for p<0.05.

Results.

Preliminary data on rectification and NASPM provide good proof that CPARs are formed in the SNI group (FIG. 2). We will examine the presence of CPARs in the PI model using the same strategy.

Example 5

GluA1 Upregulation in the NAc Reduces Depression-Like Behavior in Postoperative Pain States Using SNI and PI Models Pharmacologic block of CPARs and genetic inhibition of synaptic GluA1 expression in NAc neurons may increase depression-like behavior in SNI and PI models. Antagonism of CPARs and Inhibition of GluA1 expression at the synapses of NAc neurons increase depression-like behavior in postoperative pain states.

Figure 9A:
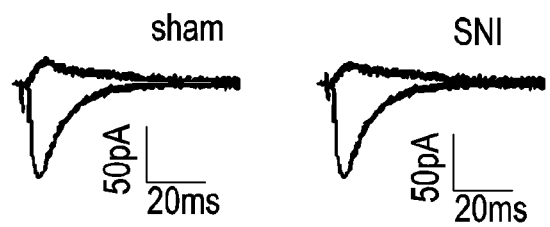
FIG. 9 demonstrates inward rectification of EPSCs in MSNs from SNI-treated rats. (A) Evoked EPSCs recorded at +40 mV and −70 mV in sham and SNI-treated rats. (B) I-V relationship of EPSCs recorded in neurons from sham and SNI groups. Note the inward rectification of EPSCs from SNI-treated rat compared with sham control. (C) Averaged rectification index from sham- and SNI-treated rats. Neurons recorded from SNI-treated rats show greater rectification (n=7 from 3 rats in each group). ***P<0.001, student's t test.
Figure 9B:
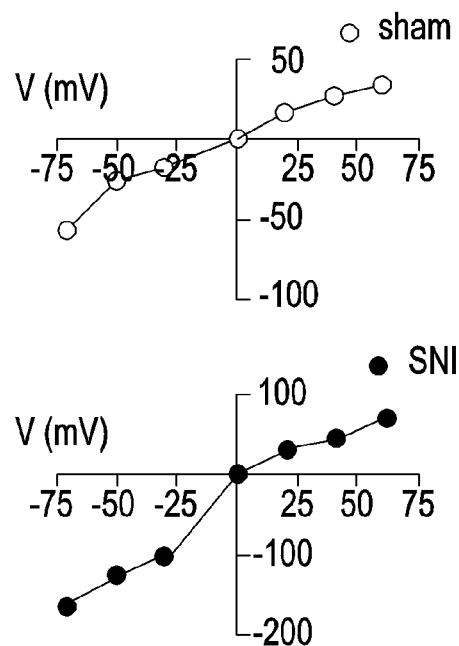
Figure 9C:
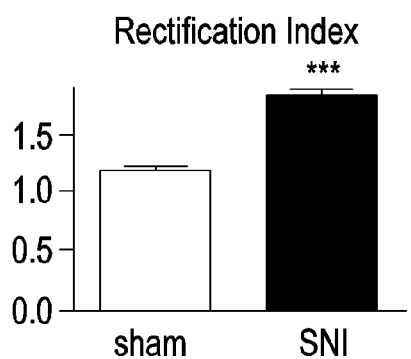

GluA1 signaling in the NAc has been suggested to protect against depression. For example, decreased GluA1 levels in the NAc are found in rat depression models, and GluA1 knockout mice perform poorly on learned helplessness test, an assay for depression (Toth, et al., *J. Neurochem* 2008; 107: 522-32; Chourbaji, et al., *FASEB J* 2008; 22: 3129-34). Meanwhile, antidepressant treatment increases GluA1 levels in the NAc (Tan, et al. *Exp Brain Res* 2006; 170: 448-56). Preliminary data suggest increased synaptic GluA1 levels and CPAR formation in pain states (FIGS. 8, 9). To understand the role of CPARs in mood regulation, CPARs will be blocked directly with NASPM, IEM 1460 and 6-cyano-7-nitroquinoxaline-2,3-dione (CNQX). GluA1 trafficking machinery will be blocked with a construct in which the C terminus of GluA1 is fused to GFP (GFP-GluA1-ct) (Rumpel, et al., *Science* 2005; 308: 83-8; Mitsushima, et al., *Proc Natl Acad Sci USA* 2011; 108: 12503-8). Pharmacologic blockers provide specificity for CPARs, but the genetic blocker directly assesses the role of GluA1 trafficking; hence these techniques are complementary. The effects of these inhibitors will be tested with a standard depression test—sucrose preference test (SPT)—and sensory pain tests.

Preliminary Data.

Figure 10A:
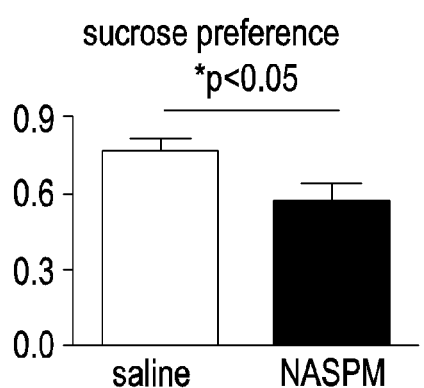
FIG. 10 demonstrates that blocking calcium permeable AMPA receptors (CPARs) in the NAc increases depression-like behavior in SNI-treated rats without altering their sensory sensitivities and locomotor activities. (A) In SNI treated rats, NASPM, a blocker for CPARs, compared with saline, reduces sucrose preference. Sucrose preference test is commonly used in rats to assess anhedonia, a key feature of depression. Higher preference for sucrose (1% solution) over water suggests normal hedonic response, whereas reduced sucrose preference suggests anhedonia. NASPM: 9 rats; saline: 10 rats. P<0.05, student's t test. (B) NASPM has no effects on mechanical hypersensitivity. NASPM: 5 rats; saline 6 rats, P=0.05. (C) NASPM has no effects on baseline locomotion. NASPM: 7 rats; saline: 4 rats. P=0.03, two way ANOVA. (D) Placement of cannuli in the NAc core showing injector tips (x).
Figure 10B:
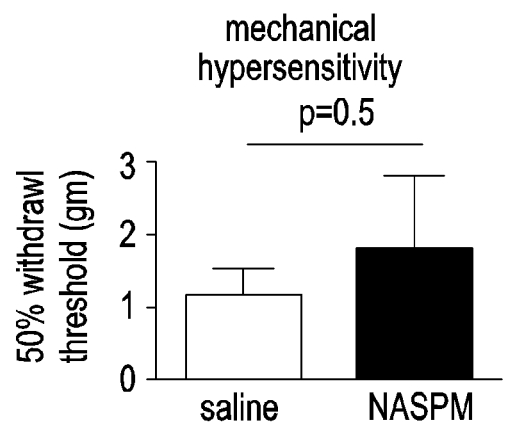
Figure 10C:
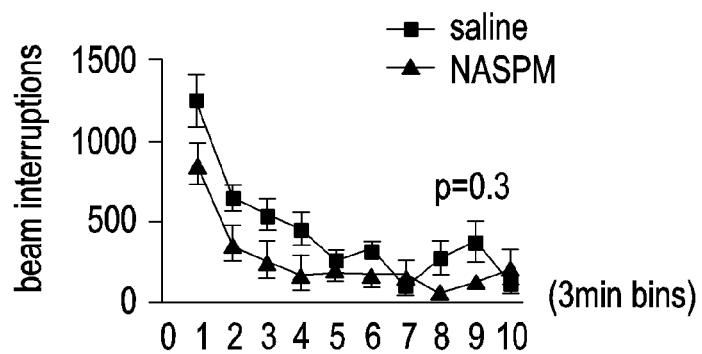

To block CPARs locally in the NAc, microcannulas were stereotactically implanted bilaterally into the NAc, a technique well established (Carr, et al., *Neuroscience* 2010; 165: 1074-86). The NAc has anatomically distinct core and shell regions, both of which are involved in mood regulation. The core region, has been shown to be sensitive to CPAR signaling from studies on cocaine (Conrad, et al., *Nature* 2008; 454: 118-21; Bachtell, et al., *Eur J Neurosci* 2008; 27: 2229-40) and other data (FIG. 9). After cannula insertion, SNI was performed to induce pain, and on POD 14, NASPM, a CPAR blocker, or saline was delivered to the NAc via the cannulas. NASPM, compared with saline, causes a statistically significant increase in depression-like behavior measured by a decrease in sucrose preference on the sucrose preference test, a classic test of depression (FIG. 10A). These results show that CPARs, in vivo, attenuate depressive symptoms of postoperative pain. In contrast, NASPM does not alter sensory hypersensitivity or locomotor activities (FIG. 10 B, C). Sensory hypersensitivity was measured using von Frey filaments (Wang, et al. *Anesthesiology* 2011; 115: 812-821), whereas locomotion tests were performed using standard protocols (Carr, et al., *Pschopharmacology* (*Berl*) 2009; 201: 495-506).

These results demonstrate the role of CPARs in controlling depression-like behavior induced by postoperative pain. From a clinical perspective, this is an exciting finding, as it provides us with a pharmacologic target for treating pain-induced depression in the postoperative period. NASPM does not change mechanical hypersensitivity, suggesting that CPARs do not control sensory symptoms of pain, in contrast to the reported anti-nociceptive effects of dopamine signaling (Gear, et al *J. Neurosci* 1999; 19: 7175-81; Altier, et al., *Brain Res* 1993; 628: 279-85). While glutamate and dopamine signaling are both critical for the function of MSNs of the NAc, these results suggest that they may have different roles in pain states.

Methods.

Test the Behavioral Consequences of Pharmacologic CPAR Block.

Figure 10D:
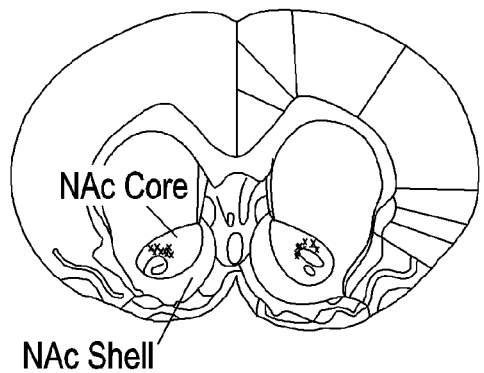
Figure 11A:
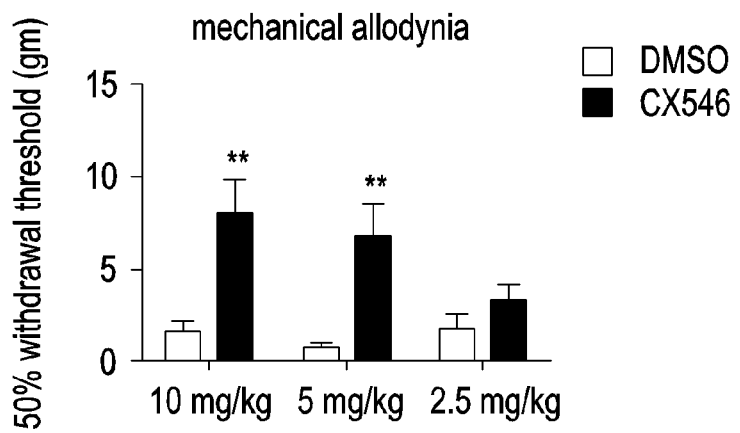
FIG. 11 demonstrates (A) intraperitoneal injections of AMPA potentiator CX546 at 5 and 10 mg/kg doses, compared with DMSO (vehicle), relieve mechanical allodynia in rats that had SNI surgery. N=7 rats for DMSO; 9 for CX546. p<0.01 for 5 and 10 mg/kg doses, two-way ANOVA with post-hoc Bonferroni test. (B) Intraperitoneal injection of AMPA potentiator CX546 at the 10 mg/kg dose, compared with DMSO (vehicle), relieves cold allodynia in rats that had SNI surgery. N=7 rats for DMSO; 9 for CX546. p<0.05, two-way ANOVA with post-hoc Tukey test. (C) Intraperitoneal injection of AMPA potentiator CX546 (10 mg/kg), compared with DMSO (vehicle), improves performance on the forced swim test in rats that had SNI surgery. N=8-9 rats. p<0.05, Student's t test.
Figure 11B:
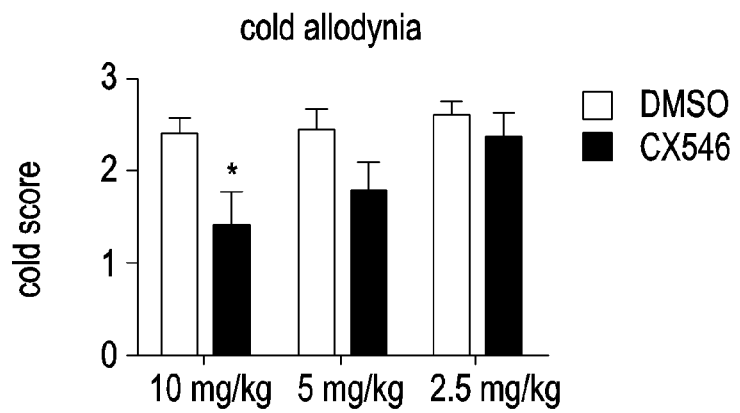
Figure 11C:
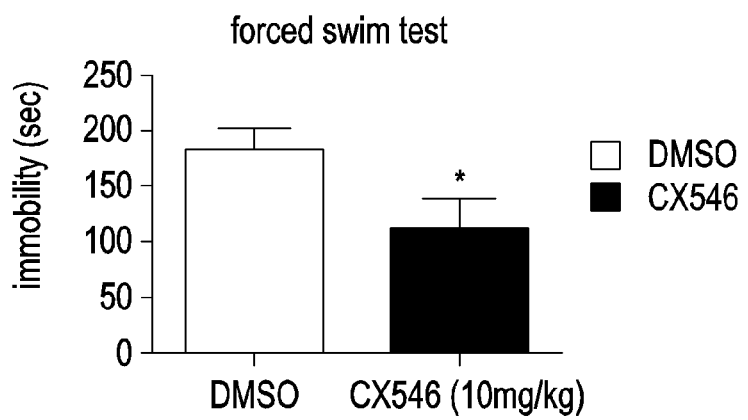

In the PI model, CPARs will be blocked with NASPM on POD 1, using the same microinjection technique outlined above. After drug delivery, SPT, mechanical hypersensitivity and locomotor tests will be performed in NASPM and control (saline) groups as shown above. After these behavioral tests, rat brains will be dissected and strained with H&E to confirm correct cannula placements. Only data from correctly placed cannulas will be used (FIG. 10D). NASPM is a highly specific blocker of CPARs, but to further verify its specificity, these studies will be repeated with IEM 1460 and CNQX in PI and SNI models. IEM 1460 is an agonist for polyamines and has similar properties as NASPM, whereas CNQX blocks both CPARs and calcium impermeable AMPA receptors. Finally, to confirm the regional specificity of drug effects, the above experiments will be repeated with microcannulas implanted in the NAc shell region and in the dorsal striatum.

Test the Behavioral Consequences of Genetic Inhibition of GluA1 Trafficking.

A genetic approach to disrupt GluA1 trafficking machinery allows selective antagonism of synaptic GluA1 expression (Rumpel, et al., *Science* 2005; 308: 83-8; Mitsushima, et al., *Proc Natl Acad Sci USA* 2011; 108: 12503-8). A peptide containing the full C terminus of GluA1 fused to GFP (GFP-GluA1-ct) in a herpes simplex vector was constructed. This peptide has been shown to occupy and block proteins required for GluA1 trafficking (Rumpel, et al., *Science* 2005; 308: 83-8; Mitsushima, et al., *Proc Natl Acad Sci USA* 2011; 108: 12503-8). GFP-GluA1-ct peptide or GFP-vehicle (control) will be injected into the NAc (POD 14 after SNI and POD1 after PI). Previous studies suggest 24 hours are needed for optimal transfection (Mitsushima, et al., *Proc Natl Acad Sci USA* 2011; 108: 12503-8), and thus rats will be subjected to depression, sensory and locomotion tests one day after injection. Transfection will be confirmed by immunofluorescent analysis of NAc slices and only use data from transfection that is spatially restricted to the NAc. The functional effects of GluA1 inhibition will be confirmed with electrophysiology (EP) by measuring EPSCs from transfected (recognized by their GFP tag) and non-transfected neurons in pain and control groups. This genetic method to disrupt GluA1 expression on GluA1 trafficking has been reported (Serulle, et al., *Neuron* 2007; 56: 670-88).

Experimental Design

1) Chronic Postoperative Pain Model

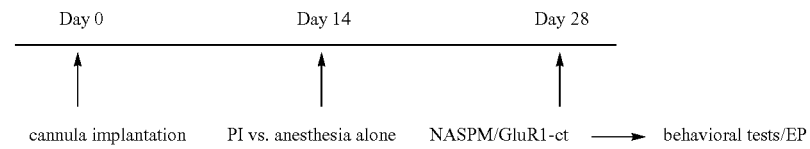

2) Acute Postoperative Pain Model

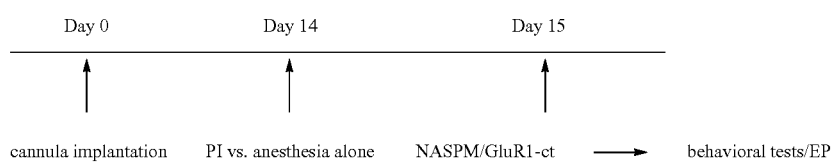

Based on preliminary data, an average difference of 0.2 in sucrose preference between NASPM and saline treatment will be observed, with a STD of 0.15. Power analysis yields n=10 per group for p<0.05. Previous data showed the average difference between depressed and control rats on the forced swim test to be 50 seconds of immobility, with a STD of 40 seconds (FIG. 6A), and power analysis yields n=10 for p<0.05.

Results.

Pharmacologic Block of CPARs Enhances Depressive Symptoms of Pain.

In the SNI model, NASPM antagonism of CPARs was shown to enhance depression-like behavior on the sucrose preference test (SPT). NASPM will have pro-depressant effects in PI treated rats. Since IEM 1460 has similar biophysical activities as NASPM, it should have similar behavioral effects. CNQX blocks CPARs (in addition to calcium impermeable AMPA receptors), and it should also enhance depressive symptoms in pain models. There will be no effects on sensory pain symptoms or locomotion with NASPM, IEM 1460 or CNQX. CNQX is known not to alter locomotion (Maj, et al., *Pol J Pharmacol* 1995; 47: 269-77). GluA1 upregulation is an activity dependent event, and in the absence of pain, control rats are unlikely to express high levels of CPARs (FIG. 9). Therefore, there will be no pro-depressant effects of NASPM, IEM 1460 or CNQX in control groups.

Genetic Inhibition of CPARs Enhances Depressive Symptoms of Pain.

GFP-GluA1-ct antagonizes the trafficking of GluA1 subunits to the synapse, and this construct should decrease synaptic GluA1 expression and enhance depression-like behavior in pain but not in control groups. We do not anticipate a change in locomotion or sensory hypersensitivity with GFP-GluA1-ct transfection. On immunostaining, transfection of GFP-GluA1-ct in neurons is expected in the NAc core only. On electrophysiology recordings, there will be reduced EPSCs in neurons transfected with GFP-GluA1-ct compared with nontransfected neurons in the pain group, similar to a previous report (Rumpel, et al., *Science* 2005; 308: 83-8).

Example 6

Pharmacologic Potentiation of CPAR Currents in NAc Neurons with Ampakines Treats Depression If blocking CPARs increases depressive symptoms, potentiating CPAR currents may reduce depression-like behavior in postoperative pain states. CPARs attenuate depressive symptoms of pain, a natural adaptive mechanism. This mechanism can be pharmacologically enhanced. AMPA potentiators, known as ampakines, are a class of compounds that increase AMPA receptor currents by slowing the deactivation of open channels (Lynch, et al., *Trends Neurosci* 2006; 29: 554-62; Jin, et al., *J Neurosci* 2005; 25: 9027-36; Vyklicky, et al., *Neuron* 1991; 7: 971-84). These compounds only potentiate currents through already open channels, and this activity dependent feature provides greater therapeutic specificity with a better side effect profile (O'Neill, et al. *Curr Drug Targets* 2007; 8: 603-20; Simmons, et al., *Proc Natl Acad Sci USA* 2009; 106: 4906-11; Goff, et al., *Neuropsychopharmacology* 2008; 33: 465-72). Some ampakines are in clinical trial for depression (O'Neill, et al. *Curr Drug Targets* 2007; 8: 603-20), but none has been studied in the postoperative period. An ampakine that potentiates CPARs specifically in the postoperative period should amplify their antidepressant effects with potentially few side effects. 2-pyrrolidinone is an ampakine that has been shown to specifically increase CPAR currents (Nishizaki, et al., *Brain Res Mol Brain Res* 2002; 98: 130-4). Thus, we will test the antidepressant effects of this compound by direct administration into the NAc via microcannulas using our pain models. This investigation will provide a very high clinical impact, by establishing a new drug to treat the depressive symptoms of postoperative pain.

Methods.

We will use the same experimental setup as described above. After pain induction, we will inject 2-pyrrolidinone or saline (control) bilaterally into the NAc via pre-implanted microcannulas followed by behaviors tests (SPT, mechanical hypersensitivity and locomotion). 2) While 2-pyrrolidinone has been shown in vitro to be a specific potentiator of CPARs (Nishizaki, et al., *Brain Res Mol Brain Res* 2002; 98: 130-4), we will verify the specificity of 2-pyrrolidinone by measurements of EPSCs in NAc slices from pain and control groups (see aim 1B). Power analysis: see analysis in aim 2A.

Results and Anticipated Results.

2-pyrrolidinone indeed increased sucrose in SNI- or PI-treated rats (FIG. 4). It did not have any effect on the sensory symptoms of pain, as expected. Based on this data, we expect 2-pyrrolidinone to have antidepressant effects in PI-treated rats as well. 2-pyrrolidinone has been shown to specifically increase CPAR currents (Nishizaki, et al., *Brain Res Mol Brain Res* 2002; 98: 130-4). In acute NAc slices, 2-pyrrolidinone, compared with saline (control), will increase mEPSCs recorded from rats in pain groups, but not the controls, which do not express large numbers of CPARs. Ampakines have been reported to exhibit increased effect with repeated administrations (Simmons, et al., *Proc Natl Acad Sci USA* 2009; 106: 4906-11). Two other well studied ampakines are 4-[2-(phenylsulfonylamino)ethylthio]-2,6-difluorophenoxyacetamide (PEPA) (Sekiguchi, et al., *Br J. Pharmacol* 2002; 136: 1033-41) and LY451646 (Quirk, et al *CNS Drug Rev* 2002; 8: 255-82). PEPA and LY451646 potentiate both CPARs and calcium impermeable AMPA receptors, and both drugs have antidepressant effects (Sekiguchi, et al., *Br J. Pharmacol* 2002; 136: 1033-41; Quirk, et al *CNS Drug Rev* 2002; 8: 255-82). While these compounds have not been studied in the postoperative pain state, they will be efficacious in treating the depressive symptoms of pain. These ampakines may also be administered in combination with another antidepressant such as low-dose ketamine which has been shown to have antidepressant properties in the SNI model (Wang, et al. *Anesthesiology* 2011; 115: 812-821). Interestingly, ketamine has also been shown to increase GluA1 levels (Li, et al., *Science* 2010; 329: 959-64). We will test if ampakines and ketamine have synergistic antidepressant effects.

Example 7

Systemic administration of an AMPA potentiator, CX546, commercially available, has potent analgesic effects in addition to antidepressant effects. We determined that the commercially available ampakine, CX546, can provide antidepressant effects in the chronic pain state. Furthermore, we determined that this compound has analgesic effects.

Materials and Methods

Animals

All procedures in this study were approved by the New York University School of Medicine Institutional Animal Care and Use Committee (IACUC) as consistent with the National Institute of Health (NIH) *Guide for the Care and*

*Use of Laboratory Animals* (publication number 85-23) to ensure minimal animal use and discomfort. Male Sprague-Dawley rats were purchased from Taconic Farms, Albany, N.Y. and kept in the Mispro Animal Facility in the Alexandria Life Sciences Building (New York, N.Y.), with controlled humidity, room temperature, and a 12-hour (6:30 AM to 6:30 PM) light-dark cycle. Food and water were available ad libitum. Animals arrived to the animal facility at 250 to 300 grams and were given on average 10 days to adjust to the new environment prior to the onset of any experiments.

Spared Nerve Injury (SNI) Surgery

The Spared Nerve Injury (SNI) surgery was previously described in detail (Wang et al. *Anesthesiology* 2011, 115: 812-821). Briefly, under Isoflurane anesthesia (1.5 to 2%), the skin on the lateral surface of the right thigh of rat was incised and a section made through the biceps femoris muscle to expose three branches of the sciatic nerve: sural, common peroneal and tibial nerves. The common peroneal and tibial nerves were tied with non-absorbent 5.0 silk sutures at the point of trifurcation. The nerves were then cut distal to the knot, and about 3 to 5 mm of the distal ends were removed. Muscle layer was then sutured close, while skin was stapled. Staples were removed prior to behavioral testing.

Animal Behavioral Tests

Mechanical Allodynia Testing:

A traditional Dixon up-down method with von Frey filaments was used to measure mechanical allodynia (Wang et al. *Anesthesiology* 2011, 115: 812-821). In brief, rats were individually placed into plexiglass chambers over a mesh table and acclimated for 20 min before the onset of examination. Beginning with 2.55 g, von Frey filaments in a set with logarithmically incremental stiffness (0.45, 0.75, 1.20, 2.55, 4.40, 6.10, 10.50, 15.10 g) were applied to the lateral ⅓ of right paws (in the distribution of the sural nerve) of animals at least 14 days after SNI surgery, and observers were blinded to the test conditions (CX546 vs. DMSO treatments).

Cold Allodynia Testing:

Animals were individually placed into plexiglass chambers as above and acclimated for 20 min. A drop of acetone was applied to the lateral plantar surface of the paws (in the distribution of the sural nerve). As previously described (Wang et al. *Anesthesiology* 2011, 115: 812-821), the following scoring system was applied. 0: no visible response or startle response lasting <0.5 second; 1: paw withdrawal lasting <5 seconds; 2: withdrawal lasting 5 to 10 seconds, +/− licking of the paws; 3: prolonged repetitive withdrawal lasting >10 s. Acetone was applied 5 times to each paw, and an average score was calculated. Cold allodynia tests were typically done after mechanical allodynia tests on the same day, and observers were blinded to the test conditions (CX546 vs. DMSO treatments).

Forced Swim Test:

On the first session of the test, each animal was placed for fifteen minutes into a standard clear Porsolt chamber with water at 25° C. filled to 25 cm. Afterwards, the animal was taken out of the chamber, dried and put back in its home cage. 24 hours later, the animal was placed into the Porsolt chamber again under the same conditions for 5 min. Both sessions were videotaped, but only the second session was analyzed. Immobility was defined as a lack of movement of the hind paws lasting greater than 1 second. Two independent observers, examined and graded the total time of immobility for each rat, and the average grade was presented for each animal. FST was conducted 14 days after surgeries. For data analysis, observers were blinded to the test conditions (CX546 vs. DMSO treatments). All behavior tests were done 30 minutes after drug treatment.

Statistics

The results of behavioral experiments were given as mean±SEM. For mechanical and cold allodynia assays, a two-way ANOVA with post hoc multiple pair-wise comparison Bonferroni tests was used to compare the 50% mechanical withdrawal threshold as well as cold score on the injured legs of SNI animals. An unpaired two-tailed Student's t test was used to compare the performances on the forced swim tests of CX546 and DMSO treatment groups. For all tests, a p value <0.05 was considered statistically significant. All data were analyzed using GraphPad Prism Version 5 software (GraphPad, La Jolla, Calif.).

Results

Systemic administration of an AMPA potentiator, CX546, which is commercially available, has potent analgesic effects in addition to antidepressant effects. It was previously shown that SNI surgery leads to mechanical and cold allodynia—sensory indices for pain, and increased immobility during forced swim test—index for depression (Wang et al. *Anesthesiology* 2011, 115: 812-821). Here, the analgesic and antidepressant property of CX546 was tested in rats which had undergone SNI (surgery was performed at 14 days prior to testing). The data show that compared with DMSO (vehicle) treatment, intraperitoneal administration of CX546 at 5 or 10 mg/kg doses, successfully relieves mechanical allodynia (p<0.01 for 5 and 10 mg/kg doses, two-way ANOVA with post-hoc Bonferroni test). CX546 at 10 mg/kg also relieves cold allodynia (p<0.05, two-way ANOVA with post-hoc Tukey test). At a lower dose (2.5 mg/kg), in contrast, CX546 does not produce any statistically significant analgesic effect. In addition, at 10 mg/kg, CX546 significantly decreases immobility measure on the forced swim test (p<0.05, Student's t test). These results demonstrate that CX546, which is a highly selective and relatively potent AMPA potentiator, has potent analgesic and antidepressant properties in the chronic pain state.

We claim:

1. A method of inducing analgesia in a subject comprising administering a pharmaceutically effective amount of 2-pyrrolidinone, 4-[2-(phenylsulfonylamino)ethylthio]-2,6-difluorophenoxyacetamide (PEPA), LY451646, or CX546.

2. A method according to claim 1 wherein the subject is suffering from acute, chronic or postoperative pain.

3. A method according to claim 1 wherein the 2-pyrrolidinone, 4-[2-(phenylsulfonylamino)ethylthio]-2,6-difluorophenoxyacetamide (PEPA), LY451646, or CX546 is administered in combination with one or more other analgesics or pain medications.

4. A method of treating pain comprising administering a pharmaceutically effective amount of 2-pyrrolidinone, 4-[2-(phenylsulfonylamino)ethylthio]-2,6-difluorophenoxyacetamide (PEPA), LY451646, or CX546.

5. A method according to claim 4 wherein the pain is acute, chronic or postoperative pain.

6. A method according to claim 4 wherein the 2-pyrrolidinone, 4-[2-(phenylsulfonylamino)ethylthio]-2,6-difluorophenoxyacetamide (PEPA), LY451646, or CX546 is administered in combination with one or more other analgesics or pain medications.

* * * * *

UNITED STATES PATENT AND TRADEMARK OFFICE
CERTIFICATE OF CORRECTION

PATENT NO. : 10,702,513 B2  
APPLICATION NO. : 14/401202  
DATED : July 7, 2020  
INVENTOR(S) : Jing Wang and Edward Ziff Page 1 of 1

It is certified that error appears in the above-identified patent and that said Letters Patent is hereby corrected as shown below:

In the Specification

Column 1, Line 16:
Please insert:
--GOVERNMENT SUPPORT
This invention was made with government support under R01 AR056672, TR000038, and R01 AR054897 awarded by the National Institutes of Health. The government has certain rights in the invention.--.

Signed and Sealed this
Twenty-second Day of April, 2025

Coke Morgan Stewart
*Acting Director of the United States Patent and Trademark Office*